US012054771B2

(12) United States Patent
Saghbini et al.

(10) Patent No.: US 12,054,771 B2
(45) Date of Patent: *Aug. 6, 2024

(54) METHODS OF DETERMINING NUCLEIC ACID STRUCTURAL INFORMATION

(71) Applicant: BioNano Genomics, Inc., San Diego, CA (US)

(72) Inventors: Michael G. Saghbini, San Diego, CA (US); Henry B. Sadowski, San Diego, CA (US); Goran Pljevaljcic, San Diego, CA (US); Alex R. Hastie, San Diego, CA (US); Han Cao, San Diego, CA (US)

(73) Assignee: Bionano Genomics, Inc., San Diego, CA (US)

( * ) Notice: Subject to any disclaimer, the term of this patent is extended or adjusted under 35 U.S.C. 154(b) by 362 days.

This patent is subject to a terminal disclaimer.

(21) Appl. No.: 15/117,699

(22) PCT Filed: Feb. 17, 2015

(86) PCT No.: PCT/US2015/016194
§ 371 (c)(1),
(2) Date: Aug. 9, 2016

(87) PCT Pub. No.: WO2015/126840
PCT Pub. Date: Aug. 27, 2015

(65) Prior Publication Data
US 2016/0369331 A1   Dec. 22, 2016

Related U.S. Application Data

(60) Provisional application No. 61/941,261, filed on Feb. 18, 2014.

(51) Int. Cl.
| *C12Q 1/68* | (2018.01) |
| *C12Q 1/6869* | (2018.01) |
| *G16B 20/00* | (2019.01) |
| *G16B 20/30* | (2019.01) |

(52) U.S. Cl.
CPC ........... *C12Q 1/6869* (2013.01); *G16B 20/00* (2019.02); *G16B 20/30* (2019.02)

(58) Field of Classification Search
CPC ............ C12Q 1/6869; C12Q 2521/125; C12Q 2563/107; C12Q 2539/113
See application file for complete search history.

(56) References Cited

U.S. PATENT DOCUMENTS

| 6,875,750 B1 | 4/2005 | Pignot et al. |
| 7,217,562 B2 | 5/2007 | Cao et al. |
| 7,670,770 B2 | 3/2010 | Chou et al. |
| 7,960,105 B2 | 6/2011 | Schwartz et al. |
| 8,008,007 B2 | 8/2011 | Weinhold et al. |
| 8,192,106 B2 | 3/2012 | Weinhold et al. |
| 10,633,706 B2 | 4/2020 | Ebenstein et al. |
| 2004/0033515 A1 | 2/2004 | Cao et al. |
| 2006/0275911 A1 | 12/2006 | Wang et al. |
| 2008/0206760 A1* | 8/2008 | Berlin ................. C12Q 1/6827 435/6.16 |
| 2011/0306504 A1 | 12/2011 | Xiao et al. |
| 2012/0097835 A1 | 4/2012 | Sharonov |
| 2012/0237936 A1 | 9/2012 | Xiao et al. |
| 2012/0244635 A1 | 9/2012 | Austin et al. |
| 2013/0072386 A1* | 3/2013 | Xiao ................. G01N 33/5302 506/38 |
| 2013/0177902 A1 | 7/2013 | Xiao et al. |
| 2014/0221218 A1* | 8/2014 | Cao ..................... C12Q 1/6869 435/6.1 |

FOREIGN PATENT DOCUMENTS

| CN | 102292451 | 12/2011 | |
| WO | WO2010002883 | 1/2010 | |
| WO | WO-2010002883 A2 * | 1/2010 | ........... C12Q 1/6818 |
| WO | WO-2010102257 A2 * | 9/2010 | ......... C12N 15/1079 |
| WO | WO-2011150475 A1 * | 12/2011 | ........... C12Q 1/6841 |
| WO | WO 2013036860 | 3/2013 | |
| WO | WO-2014043763 A1 * | 3/2014 | ........... C12Q 1/6806 |

OTHER PUBLICATIONS

Lam, Ernest T., et al. "Genome mapping on nanochannel arrays for structural variation analysis and sequence assembly." Nature biotechnology 30.8 (2012): 771. (Year: 2012).*
Tatton et al.( Annals of neurology 44.S1 1 (1998): S142-S148.). (Year: 1998).*
Moore et al.(DNA Methylation and Its Basic Function. Neuropsychopharmacol 38, 23-38 (2013); published online Jul. 11, 2012) (Year: 2013).*
Fujita, Pauline A., et al. "The UCSC genome browser database: update 2011." Nucleic acids research 39.suppl_1 (2010): D876-D882. (Year: 2010).*
Lukinavičius et al.(Targeted labeling of DNA by methyltransferase-directed transfer of activated groups (mTAG). Journal of the american chemical society 129.10 (2007): 2758-2759 (Year: 2007).*
Lukinavičius 2007 supplementary materials (Year: 2007).*

(Continued)

*Primary Examiner* — Sahana S Kaup

(74) *Attorney, Agent, or Firm* — Sheppard, Mullin, Richter & Hampton LLP

(57) ABSTRACT

Methods of double-stranded nucleic acid sequence determination and assembly that are able to identify insertions, deletions, repeat region sizes and genomic rearrangements, for example, are disclosed herein, which can use relatively large labeled nucleic acid fragments to analyze the structure of even larger genetic regions. In some embodiments these methods involve the use of certain parameters which unexpectedly improve overall method performance. In some embodiments these methods involve sample labeling that does not result in the formation of single-stranded nucleic acid fragment labeling intermediaries.

22 Claims, 6 Drawing Sheets

(56) References Cited

OTHER PUBLICATIONS

Calladine et al., "Understanding DNA: The Molecule and How it Works," Academic Press 2004.
Cao et al., "Luminescence enhancement of core-shell ZnS:Mn/ZnS nanoparticles," Applied Physics Letters 2002, 80(23), 4300-4302.
Cao et al., "Growth of aligned carbon nanotubes on self-similar macroscopic templates." Applied Physics Letters 2002, 81(7), 1297-1299.
Comstock & Rajski "Conversion of DNA methyltransferases into azidonucleosidyl transferases via synthetic cofactors," Nucleic Acids Research 2005, 33(5), 1644-1652.
Das et al., "Single molecule linear analysis of DNA in nano-channel labeled with sequence specific fluorescent probes," Nucleic Acids Research 2010, 38(18), e177, in 8 pages.
Dalhoff et al., "Direct transfer of extended groups from synthetic cofactors by DNA methyltransferase," Nature Chemical Biology 2006, 2(1), 31-32.
Hastie et al., "Rapid Genome Mapping in Nanochannel Arrays for Highly Complete and Accurate De Novo Sequence Assembly of the Complex *Aegilops tauschii* Genome," PLOS One 2013, 8(2), e55864, in 10 pages.
International Preliminary Report of Patentability dated Aug. 23, 2016 in PCT Patent Application No. PCT/US2015/016194.
International Search Report and Written Opinion dated Jun. 8, 2015 in PCT Patent Application No. PCT/US2015/016194.
Kim et al., "Enzymatically Incorporated Genomic Tags for Optical Mapping of DNA-Binding Proteins," Angew. Chem. Int. Ed. 2012, 51, 3578-3581.
Kriukienė et al., "DNA unmethylome profiling by covalent capture of CpG sites," Nature Communications 2013, 4(2190), 1-10.
Lam et al., "Genome mapping on nanochannel arrays for structural variation analysis and sequence assembly," Nature Biotechnology 2012, 30(8), 771-776.
Lukinavicius et al., "Engineering the DNA cytosine-5 methyltransferase reaction for sequence-specific labeling of DNA," Nucleic Acids Research 2012, 40(22), 11594-11602.
Lukinavicius et al., "Targeted Labeling of DNA by Methyltransferase-Directed Transfer of Activated Groups (mTAG)," J. Am. Chem. Soc. 2007, 129, 2758-2759.
Office Action dated Mar. 11, 2019 received in Chinese Patent Application No. 201580009351.1.
Office Action dated Oct. 12, 2019 received in Chinese Patent Application No. 201580009351.1.
Office Action dated May 7, 2020 received in Chinese Patent Application No. 201580009351.1.
Pljevaljčić et al., "Sequence-specific Methyltransferase-Induced Labeling of DNA (SMILing DNA)," ChemBioChem May 2004, 251-257.
Ronen et al., "SEQuel: improving the accuracy of genome assemblies," Bioinformatics 2012, 28, i188-i196.
Schatz et al., "The DNA60IFX contest," Genome Biology 2013, 14(124), in 4 pages.
Tatton et al., "A Fluorescent Double-Labeling Method to Detect and Confirm Apoptotic Nuclei in Parkinson's Disease," American Neurological Association 1998, 44(1), S142-S148.
Tegenfeldt et al., "The dynamics of genomic-length DNA molecules in 100-nm channels," PNAS 2004, 101(30), 10979-10983.
Valouev et al., "An algorithm for assembly of ordered restriction maps from single DNA molecules," PNAS 2006, 103(43), 15770-15775.
Wendl & Wilson, "Aspects of coverage in medical DNA sequencing," BMC Bioinformatics 2008, 9(239), in 11 pages.
Non-Final Office Action dated Nov. 27, 2020 in U.S. Appl. No. 16/909,884.
Notice of Allowance dated Nov. 9, 2020 in Chinese Patent Application No. 201580009351.1.
Final Office Action dated Mar. 12, 2021 in U.S. Appl. No. 16/909,884.
Non-Final Office Action dated Dec. 24, 2021 in U.S. Appl. No. 16/909,884.

\* cited by examiner

METHODS OF DETERMINING NUCLEIC ACID STRUCTURAL INFORMATION

RELATED APPLICATIONS

This application is the US national phase of PCT Application No. PCT/US2015/016194, filed Feb. 17, 2015, which claims priority under 35 U.S.C. § 119(e) to U.S. Provisional Application No. 61/941,261 filed on Feb. 18, 2014. The entire content of these related applications are expressly incorporated herein by reference in their entireties.

FIELD

The present invention relates to the field of nanotechnology, and to the fields of genome assembly and sample analysis based on single molecule visualization and analysis.

BACKGROUND

Macromolecules, such as DNA or RNA, are long polymer chains composed of nucleotides, whose linear sequence is directly related to the genomic and post-genomic gene expression information of the source organism. Direct sequencing and mapping of sequence regions, motifs, and functional units such as open reading frames (ORFs), untranslated regions (UTRs), exons, introns, protein factor binding sites, epigenomic sites such as CpG clusters, microRNA sites, transposons, reverse transposons and other structural and functional units are important in assessing of the genomic composition and "health profile" of individuals.

Tremendous progress has been made in the determination of local sequence information—that is, the specific sequence of bases at a local region of nucleic acid molecule. The accessibility of this information, and the relative ease and low cost with which it can be obtained, represents a great opportunity to improve human health by allowing personalized medical diagnosis.

However, methods of determining genomic sequence information currently available and in development share a common defect in that they focus upon local sequence information removed from its structural genomic context. As a result, sequence information related to genomic rearrangements, duplications, the length of repetitive regions and other structural sequence information is not easily accessed by current techniques.

In some cases, the complex rearrangement of the nucleotides' sequence, including segmental duplications, insertions, deletions, inversions and translocations, during an individual's life span leads to disease states such as genetic abnormalities or cell malignancy. In other cases, sequence differences, copy number variations (CNVs), and other differences between different individuals' genetic makeup reflects the diversity of the genetic makeup of the population and differential responses to environmental stimuli and other external influences, such as drug treatments.

Other ongoing processes such as DNA methylation, histone modification, chromatin folding, and other changes that modify DNA-DNA, DNA-RNA or DNA-protein interactions influence gene regulations, expressions and ultimately cellular functions resulting in diseases and cancer.

Genomic structural variations (SVs) are widespread, even among healthy individuals. The importance to human health of understanding genome sequence information has become increasingly apparent.

Conventional cytogenetic methods of visualizing genomic structural information, such as karyotyping or FISH (Fluorescent in situ Hybridization) provided a global view of genomic structural information down to the level of a single cell. These methods are effective in revealing gross changes of the genome such as aneuploidy, gain, loss or rearrangements of large fragments of thousands and millions of base pairs. However, these methods suffer from relatively low sensitivity and resolution in detecting medium to small sequence motifs or lesions, as well as being laborious, of limited speed and inconsistent accuracy.

More recent methods for detecting sequence regions, sequence motifs of interests and SVs, such as aCGH (array Comparative Genomic Hybridization), fiberFISH, or massive pair-end sequencing have improved resolution and throughput, but are still either indirect, laborious and inconsistent, expensive or often with limited fixed resolution, providing either inferred positional information relying on mapping back to reference genome for reassembly or comparative intensity ratio information that does not reveal balanced lesion events such as inversions or translocations.

Functional units and common structural variations are thought to encompass from tens of bases to more than megabases. Thus, a method of revealing sequence information and SVs across the resolution scale from sub-kbs to megabases along large native genomic molecules would be highly desirable in sequencing and fine-scale mapping projects of more individuals in order to catalog previously uncharacterized genomic features.

Furthermore, phenotypical polymorphism or disease states of biological systems, particularly in multiploid organisms such as humans, are consequences of the interplay between the two haploid genomes inherited from maternal and paternal lineage. Cancer is often the result of the loss of heterozygosity among diploid chromosomal lesions.

Current sequencing analysis approaches are largely based on samples derived from averaged multiploidy genomic materials with limited haplotype information. This is largely due to existing front end sample preparation methods currently employed to extract the mixed diploid genomic material from a heterogeneous cell population and then shredding them into random smaller pieces, which destroys the native structural information of the diploid genome.

Recently developed second-generation sequencing methods, though having improved throughput, further complicate the delineation of complex genomic information due to more difficult assembly from much shorter sequencing reads.

In general, short reads are harder to align uniquely within complex genomes, and additional sequence information are needed to decipher the linear order of the short target region. It was considered that the order of 25 fold sequencing coverage is needed to reach similar assembly confidence instead of 8-10 fold coverage needed in conventional BAC and shotgun Sanger sequencing (Wendl M C, Wilson R K Aspects of coverage in medical DNA sequencing, BMC Bioinformatics 2008 May 16; 9:239). This imposes further challenges sequencing cost reduction and defeats the original primary goal of dramatically reducing sequencing cost below the target USD $1000 mark.

SUMMARY

Methods, compositions and devices related to the rapid and economical determination of nucleic acid structural information are disclosed herein.

In some embodiments, the present disclosure provides methods of obtaining structural information from a DNA or other nucleic acid sample. These methods suitably include processing a double-stranded DNA sample so as to give rise to a tag such as a covalently-bound sequence specific tag at at least one location throughout a nucleic acid sample.

Note that important genetic information can be gleaned from the mere size/length of a DNA region that is flanked by two or more probes. For example, if probes are bound to a sample so as to flank a region of interest and it is seen that the region of interest is longer than is normally seen in a subject, an insertion, duplication, or other mutation is suspected. In some instances, the user will know that the subject may be disposed to a physiological condition or disease characterized by a lengthened region of interest, such as a condition characterized by excessive copy numbers of a particular gene.

Incorporation of at least one label in a sequence-specific manner may be accomplished by contacting a polynucleic acid sample with a sequence-specific methyltransferase (MTase).

An important advance relates to sequence-specific labeling, with MTase labeling being a preferred mode based on its sequence specificity, comprising conditions needed for complex genome assembly, based on our work with human and *Drosophila* genomes. The methods, compositions and systems disclosed herein permit genetic analysis of DNA or other nucleic acid biopolymer samples without having to break the biopolymer into individual nucleic acids for analysis. Moreover, the methods, compositions and systems disclosed herein enable the user to perform an analysis of a nucleic acid biopolymer that can be largely independent of the sequence of the nucleic acids within the biopolymer.

It is to be appreciated that certain features disclosed herein are, for clarity, described in the context of separate embodiments, elements, or steps; however these features may also be provided in combination in a single embodiment. Conversely, various features disclosed here that are, for brevity, described in the context of a single embodiment, may also be provided separately or in any sub-combination. Further, reference to values stated in ranges include each and every value within that range.

In some embodiments, the present disclosure includes methods of obtaining structural information from a DNA or other nucleic acid sample. These methods suitably include processing a double-stranded DNA sample so as to give rise to sequence-specific labeling of a nucleic acid molecule, such as sequence-specific labeling that may generate a 'bar code', such as a bar code indicating the relative position of specific sequences identified by a modifying enzyme. In some embodiments the modifying enzyme is a methyltransferase, and in some embodiments the modification comprises addition of a fluorophore at a region of the nucleic acid of known sequence, such as a sequence upon which a selected methyltransferase acts.

The present disclosure may be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

Some embodiments disclosed herein provide methods of characterizing a first nucleic acid sample to interrogate a genomic region, comprising: labeling a plurality of nucleic acid molecules in the first nucleic acid sample at at least one repeated motif with a first label, wherein the labeling maintains integrity of the plurality of nucleic acid molecules; marking the plurality of nucleic acid molecules in the first nucleic acid sample with a second label, wherein the second label is distinct from the first label; linearizing the plurality of nucleic acid molecules by passing the plurality of nucleic acid molecules into at least one nanochannel; detecting the first label and the second label to produce patterns of the at least one repeated motif of the plurality of nucleic acid molecules; and assembling the patterns of the at least one repeated motif of the plurality of nucleic acid molecules to construct a first map of the genomic region.

In some embodiments, the plurality of nucleic acid molecules comprises DNA. In some embodiments, said DNA comprises double-stranded DNA. In some embodiments, the plurality of nucleic acid molecules covers the entire length of the genomic region. In some embodiments, the plurality of nucleic acid molecules covers an enriched fraction of the genomic region. In some embodiments, the genomic region comprises at least two haplotypes.

In some embodiments, the first map of the genomic region is compared to a second map of the genome region. In some embodiments, said second map is of a reference genome. In some embodiments, said second map is generated from genomic sequence information. In some embodiments, said second map is independently generated. In some embodiments, said second map is generated from a second nucleic acid sample. In some embodiments, said second map comprises at least two haplotypes. In some embodiments, said second map is generated from a second nucleic acid sample from a common individual as to the first nucleic acid sample. In some embodiments, said second map is generated from a second nucleic acid sample from an individual distinct from said first nucleic acid sample. In some embodiments, said second map is from a common species as said first nucleic acid sample. In some embodiments, said second map is from a species distinct from said first nucleic acid sample. In some embodiments, said second map is generated from a tumor cell source. In some embodiments, said second map is generated from a healthy cell source. In some embodiments, said second map is generated from a mutagenized cell source. In some embodiments, said second map is generated from an unmutagenized cell source.

In some embodiments, the at least one repeated motif has an average repeat frequency of about 5 sites to about 35 sites per 100 Kb in the genomic region. In some embodiments, the at least one repeated motif has an average frequency of about 5 sites to about 25 sites per 100 Kb in the genomic region. In some embodiments, more than one repeated motifs are labeled, and each of said more than one repeated motifs is labeled with a distinct label. In some embodiments, more than one repeated motifs are labeled, and each of said more than one repeated motifs is labeled with a single label.

In some embodiments, the second label is a nonspecific nucleic acid label. In some embodiments, the second label is selected from the group consisting of Ethidium, SYBR, YOYO, TOTO, BOBO, SYPRO, SYTO, DAPI, POPO, and Hoechst.

In some embodiments, the at least one repeated motif is a methyltransferase recognition sequence, and wherein labeling is effected with a methyltransferase and a modified cofactor. In some embodiments, the modified cofactor comprises a transferable tag which becomes covalently coupled to the methyltransferase recognition sequence. In some embodiments, the modified cofactor comprises a detectable tag. In some embodiments, the transferable tag is selected form the group consisting of a fluorophore, a quantum dot, a dendrimer, a nanowire, a bead, a hapten, streptavidin, avidin, neutravidin, biotin, a stabilized reactive group a radiolabel, an electromagnetic label, an azide, Dibenzocyclooctyne (DBCO), and an alkyne. In some embodiments, the transferable tag is selected from the group consisting of an azide, Dibenzocyclooctyne (DBCO), and an alkyne. In some embodiments, the transferable tag is a fluorophore. In some embodiments, the transferable tag is Azide-DBCO. In some embodiments, the transferable tag is a quantum dot. In some embodiments, the transferable tag is an electromagnetic tag. In some embodiments, the transferable tag is detected electronically and/or electrically. In some embodiments, the modified cofactor is directly coupled to the methyltransferase recognition sequence. In some embodiments, the detectable tag is selected form the group consisting of a fluorophore, a quantum dot, a dendrimer, a nanowire, a bead, a hapten, streptavidin, avidin, neutravidin, biotin, a stabilized reactive group, a radiolabel, an electromagnetic label, an azide, Dibenzocyclooctyne (DBCO), and an alkyne. In some embodiments, the detectable tag is selected from the group consisting of an azide, Dibenzocyclooctyne (DBCO), and an alkyne. In some embodiments, the detectable tag is a fluorophore. In some embodiments, the detectable tag is Azide-DBCO. In some embodiments, the detectable tag is a quantum dot. In some embodiments, the detectable tag is an electromagnetic tag. In some embodiments, the detectable tag is detected electronically and/or electrically. In some embodiments, the first label is detectable in a visible light spectrum. In some embodiments, the first label is not detectable in a visible light spectrum. In some embodiments, the first label is detectable radiometrically. In some embodiments, the first label is detectable through its impact on a cross-current. In some embodiments, the cross current is an electromagnetic current.

In some embodiments, the at least one repeated motif includes at least one binding site for a binding entity selected form the group consisting of a non-cutting restriction enzyme, a zinc finger protein, an antibody, a transcription factor, a transcription activator like domain, a DNA binding protein, a polyamide, a triple helix forming oligonucleotide, and a peptide nucleic acid; and wherein labeling is effected with the binding entity. In some embodiments, the binding entity comprise at least one detectable tag selected form the group consisting of a fluorophore, a quantum dot, a dendrimer, a nanowire, a bead, a hapten, streptavidin, avidin, neutravidin, biotin, a stabilized reactive group, a radiolabel, an electromagnetic label, an azide, Dibenzocyclooctyne (DBCO), and an alkyne. In some embodiments, the detectable tag is selected from the group consisting of an azide, Dibenzocyclooctyne (DBCO), and an alkyne. In some embodiments, the detectable tag is a fluorophore. In some embodiments, the detectable tag is Azide-DBCO. In some embodiments, the detectable tag is a quantum dot. In some embodiments, the detectable tag is an electromagnetic tag.

In some embodiments, the labeling has an error rate ≤30%. In some embodiments, the linearizing step comprises stretching one or more of the plurality of nucleic acid molecules to about 70% to about 100% of their persistence length. In some embodiments, the labeling step has an error rate ≤30%, and the linearizing step comprises stretching one or more of the plurality of nucleic acid molecules to about 70% to about 100% of their persistence length. In some embodiments, the labeled nucleic acid molecules have a length of at least 150 kb. In some embodiments, the labeled nucleic acid molecules have a length of at least 150 kb, and wherein the labeling step has an error rate ≤30%. In some embodiments, the labeled nucleic acid molecules have a length of at least 150 kb, wherein the labeling step has an error rate ≤30%, and wherein the linearizing step comprises stretching the nucleic acid molecules between about 70% to about 100% of their persistence length. In some embodiments, the labeling step has an error rate ≤20%. In some embodiments, the labeling step has an error rate ≤15%.

In some embodiments, the nucleic acid molecules correspond to at least 20 fold coverage of the genomic region. In some embodiments, the genomic region is at least about 0.5 Mb, 0.7 Mb, 1 Mb, 1.5 Mb, 2 Mb, or larger. In some embodiments, the methods further comprise tagging the nucleic acid molecules with a third label to identify epigenomic information. In some embodiments, the methods further comprise tagging the nucleic acid molecules with a fourth label to identify any factor with a DNA binding domain. In some embodiments, the first map comprises at least one contig assembled from at least two overlapping patterns of the at least one repeated motif. In some embodiments, the first map corresponds to a fraction of a genome. In some embodiments, the first map is compared to a reference map to ascertain a similarity or difference between the first map and the reference map.

In some embodiments, the methods further comprise labeling a plurality of nucleic acid molecules in a second nucleic acid sample at the same repeated motif, wherein the labeling maintains integrity of the plurality of nucleic acid molecules; marking the plurality of nucleic acid molecules in the second nucleic acid sample with the second label; linearizing the plurality of nucleic acid molecules in the second nucleic acid sample by passing the plurality of nucleic acid molecules into at least one nanochannel; detecting the first label and the second label to produce patterns of the at least one repeated motif of the plurality of nucleic acid molecules from the second nucleic acid sample; assembling the patterns of the at least one repeated motif of the plurality of nucleic acid molecules to construct a second map of the genomic region; and comparing the first map to the second map to ascertain a similarity or difference between the first nucleic acid sample and the second nucleic acid sample. In some embodiments, said second nucleic acid sample is from a common individual as to the first nucleic acid sample. In some embodiments, said second nucleic acid sample is from an individual distinct from said first nucleic acid sample. In some embodiments, said second nucleic acid sample is from a common species as said first nucleic acid sample. In some embodiments, said second nucleic acid sample is from a separate species from said first nucleic acid sample. In some embodiments, said second nucleic acid sample is from a tumor cell source. In some embodiments, said second nucleic acid sample is from a healthy cell source. In some embodiments, said second nucleic acid sample is from a mutagenized cell source. In some embodiments, said second nucleic acid sample is from an unmutagenized cell source.

In some embodiments, the methods comprise assembling the patterns of the at least one repeated motif of at least 100, at least 1,000, at least 1,000 or more nucleic acid molecules. In some embodiments, the detecting the first label and the second label to produce patterns of the at least one repeated motif of the plurality of nucleic acid molecules is performed on a single microfluidic chip. In some embodiments, the detecting the first label and the second label to produce patterns of the at least one repeated motif of the plurality of nucleic acid molecules is performed in less than 2 hours, less than 1 hour, less than 30 minutes, less than 20 minutes, less than 10 minutes, less than 5 minutes, less than 1 minute, less than 30 seconds, less than 20 seconds, less than 10 seconds, less than 5 seconds, or less than 1 second.

Some embodiments disclosed herein provide methods of characterizing a macromolecule, comprising: labeling the macromolecule at at least one methyltransferase motif with a first label, wherein the labeling is effected with a methyltransferase and a modified cofactor, wherein the labeling maintains integrity of each strand of the macromolecule, marking the macromolecule with a non-sequence-specific label, wherein the non-sequence-specific label is distinct from the first label; linearizing the macromolecule by passing the macromolecule into at least one nanochannel; and detecting the first label and the non-sequence-specific label to identify a pattern of the at least one methyltransferase motifs characteristic of the macromolecule. In some embodiments, the macromolecule is a double-stranded DNA molecule.

Some embodiments disclosed herein provide methods of analyzing a macromolecule for a sequence structure, the method comprising the steps of: a) introducing a first label at a plurality of occurrences of a recognition site of the macromolecule, wherein no phosphodiester bond is broken through said introducing the first label to the double stranded DNA molecule; b) labeling the macromolecule with a second label; c) passing the macromolecule into a nanochannel to hold the macromolecule in an elongated state; d) detecting the first label to identify a pattern of the recognition site; and e) detecting the second label. In some embodiments, said introducing the first label comprises contacting said macromolecule with a molecule having methyltransferase activity. In some embodiments, the second label is a non-sequence-specific label. In some embodiments, the macromolecule is a double-stranded DNA molecule. In some embodiments, the second label binds double-stranded DNA breaks. In some embodiments, the first label is a fluorescent label. In some embodiments, the second label is a fluorescent label. In some embodiments, the macromolecule is held in suspension within the nanochannel.

Some embodiments disclosed herein provide methods of assaying for macromolecule identity comprising the steps of: a) labeling a macromolecule with a first label in a sequence-specific fashion without breaking the macromolecule; b) nonspecifically labeling the macromolecule; and c) obtaining information indicating a spatial relationship among the sequences labeled with the first label within the macromolecule. In some embodiments, the methods further comprise obtaining signal intensity information for a plurality of the first labels. In some embodiments, the methods further comprise comparing said spatial relationship with a predicted or observed spatial relationship in a second macromolecule. In some embodiments, the second macromolecule has a known sequence. In some embodiments, the second macromolecule is of a known source. In some embodiments, the macromolecule is a nucleic acid fragment. In some embodiments, the specific sequence occurs at a repeat frequency of 5-35 times per 100 kb in the nucleic acid fragment. In some embodiments, the specific sequence occurs at a repeat frequency of 5-25 times per 100 kb in the nucleic acid fragment. In some embodiments, the specific sequence occurs at a repeat frequency of 7-15 times per 100 kb in the nucleic acid fragment. In some embodiments, the labeling step has an error rate of at most 30%. In some embodiments, the labeling step has an error rate of at most 20%. In some embodiments, the labeling step has an error rate of at most 15%.

In some embodiments, the methods further comprise stretching the macromolecule into an elongated configuration. In some embodiments, said stretching comprises a stretch factor of at least 70% of a persistence length of said macromolecule. In some embodiments, said stretching comprises a stretch factor of at least 80% of a persistence length of said macromolecule. In some embodiments, said stretching comprises a stretch factor of not more than 85% of a persistence length of said macromolecule. In some embodiments, said stretching comprises a stretch variability of less than 20%. In some embodiments, the nucleic acid fragment is ≥150 kb. In some embodiments, the nucleic acid fragment is ≥180 kb. In some embodiments, said labeling comprises breaking a phosphodiester bond of said macromolecule. In some embodiments, said labeling does not comprise breaking a phosphodiester bond of said macromolecule. In some embodiments, said labeling comprises contacting said macromolecule with a methyltransferase.

DETAILED DESCRIPTION

Figure 1:
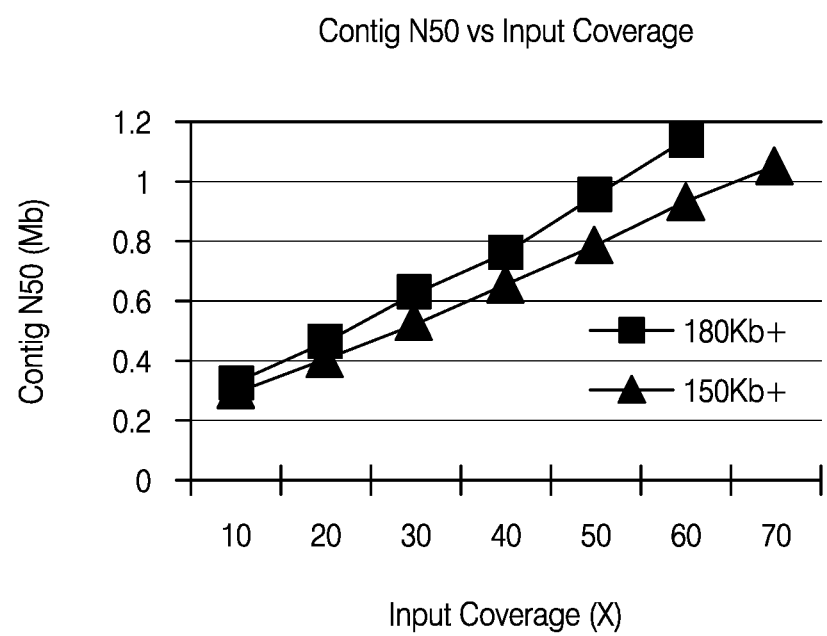
FIG. 1 depicts contig N50 in Megabases as a function of fold input coverage for samples having a minimum fragment size of 150 kb and 180 kb. Contig N50 is a measurement of distribution of contig size where total length of contigs with size >N50 is half of the total contig length. Total contig length=sum of consensus length of all contigs.

The present disclosure provides, inter alia, methods of labeling and analyzing marked features along at least one macromolecule such as a linear biopolymer, and particularly to a method of mapping the distribution and frequency of specific sequence motifs or chemical or proteomic modification state of such sequence motifs along individual unfolded nucleic acid molecules, the results of which depend on length and sequence composition of the motif. Some methods relate to using methyltransferase to label specific nucleic acid positions based on sequence at a position. Some methods relate to specific parameters for which analysis of a given labeled nucleic acid, in comparison to a reference molecule or reference data set, may be performed at an increased level of success. Some methods relate to the use of at least one specific parameter for which assembly of a given labeled nucleic acid into a larger contig may be performed at an increased level of success.

Single molecule level analysis of large intact genomic molecules provides the possibility of preserving the accurate native genomic structures by fine mapping the sequence motifs in situ without clonal processes or amplification. The larger the genomic fragments are, the less complex the sample population in genomic analytes needs to be. In an ideal scenario, only 46 chromosomal fragments need to be analyzed at single molecule level to cover the entire diploid human genome; the sequence derived from such approach has intact haplotype information by its nature.

At a practical level, megabase genomic fragments can be extracted from cells and preserved for direct analysis, which would dramatically reduce the burden of complex algorithm and assembly, and also co-relates genomic and/or epigenomic information in its original context more directly to individual cellular phenotypes.

Macromolecules suitable for the present method include polynucleotides, polynucleosides, natural and synthetic polymers, natural and synthetic copolymers, dendrimers, surfactants, lipids, natural and synthetic carbohydrates, natural and synthetic polypeptides, natural and synthetic proteins, or any combination thereof. Nucleic acid polymers, such as DNA, RNA, are contemplated as suitable macromolecules for the methods in the present disclosure. DNA is considered a particularly suitable macromolecule that can be analyzed according to the methods as discussed elsewhere herein. Macromolecules such as genomic DNA are often in the form of semi-flexible worm-like polymeric chains that are normally found as random coil configuration in free solution. For unmodified dsDNA in biological solution, its persistence length, a parameter defining its rigidity, is typically about 50 nm.

In order to achieve the consistent separation of the marked features along large intact macromolecules for quantitative measurements, one approach is to stretch such polymeric molecules in consistent linear form, either on flat surface, chemically or topologically predefined surface patterns, preferably long nanotracks or confined micro/nanochannels.

Methods of stretching and elongate long genomic molecules have been demonstrated, either by using external force such as optical tweezers, liquid-air boundary convective flows (combing), or laminar fluidic hydrodynamic flow.

Elongated forms of molecules are stabilized transiently as long as the external force is maintained or more permanently by attaching to a surface enhanced via modification with electrostatic or chemical treatment. More recently, the present inventors have demonstrated elongation of polymeric macromolecules inside micro/nanochannels by physical entropic confinement (see Cao et al, Applied Phys. Lett. 2002a, which is hereby explicitly incorporated by reference in its entirety, Cao et al, Applied Phys. Lett. 2002b, which is hereby explicitly incorporated by reference in its entirety, and U.S. Pat. No. 7,670,770, "Nanochannel arrays and their preparation and use for high throughput macromolecular analysis," issued Mar. 2, 2010, which is hereby explicitly incorporated by reference in its entirety).

A number of methods and devices relevant to these processes have been disclosed, for example "Nanochannel arrays and near-field illumination devices for polymer analysis and related methods," US Publication No. 2012/0244635 A1, published Sep. 27, 2012, which is hereby explicitly incorporated by reference in its entirety, "Methods and related devices for single molecule whole genome analysis," US Publication No. 2013/0177902 A1, published Jul. 11, 2013, which is hereby explicitly incorporated by reference in its entirety, "Methods and related devices for single molecule whole genome analysis," US Publication No. 2012/0237936 A1, published Sep. 20, 2012, which is hereby explicitly incorporated by reference in its entirety, "Method and apparatus for molecular analysis using nanostructure-enhanced Raman spectroscopy," US Publication No. 2006/0275911 A1, published Dec. 7, 2006, which is hereby explicitly incorporated by reference in its entirety, "Gradient structures interfacing microfluidics and nanofluidics, methods for fabrication and uses thereof," US Publication No. 2004/0033515 A1, published Feb. 19, 2004, which is hereby explicitly incorporated by reference in its entirety, "Polynucleotide mapping and sequencing," US Publication No. 20110306504 A1, published Dec. 15, 2011, which is hereby explicitly incorporated by reference in its entirety, and "Devices and methods for dynamic determination of sample position and orientation and dynamic repositioning," US Publication No. 2012/0097835 A1, published Apr. 26, 2012, which is hereby explicitly incorporated by reference in its entirety.

Nanochannels with diameters around 100 nm have been shown to linearize dsDNA genomic fragments up to several hundred kilobases to megabases (Tegenfeldt et al., Proc. Natl. Acad. Sci. 2004, which is hereby explicitly incorporated by reference in its entirety). Semi-flexible target molecules elongated with nanofluidics can be suspended in buffer condition within biological range of ion concentration or pH value, and hence are more amenable to performance of biological functional assays on these single molecules. This form of elongation is also relatively easier for manipulation such as moving charged nucleic acid molecules in electric field or pressure gradient in a wide range of speed from high velocity to complete stationery state with precisely controlled manner.

Furthermore, the nature of fluidic flow in a nanoscale environment precludes turbulence and many of the shear forces that would otherwise fragment long DNA molecules. This is especially valuable for macromolecule linear analysis, especially sequencing applications in which single-stranded DNA could be used. Ultimately, the read length can be only as long as the largest intact fragment that can be maintained.

Nick-labeling is an oft-employed form of sequence-specific polynucleotide labeling. An advantage of this approach is that it provides sequence specificity, which facilitates later analysis. However, a drawback of this approach is that single-stranded DNA molecules that are the temporary or final product of nick-labeling are subject to shear forces as mentioned above and elsewhere throughout the process of label visualization. Furthermore, sequence-specific nick enzymes may, if they cut frequently enough, affect both strands of a target polynucleic acid molecule in the same immediate vicinity, such that a double-stranded break is effected. Double-stranded breaks are difficult to repair and, if unrepaired, represent a loss of positional information of labels on one side of the break with respect to positional information on the other side of the break.

In addition to genomics, the field of epigenomics has been recognized as being of singular importance for its roles in human diseases such as cancer. With the accumulation of knowledge in both genomics and epigenomics, a major challenge is to understand how genomic and epigenomic factors correlate directly or indirectly to develop the polymorphism or pathophysiological conditions in human diseases and malignancies.

Whole genome analysis concept has evolved from a compartmentalized approach in which areas of genomic sequencing, epigenetic methylation analysis and functional genomics were studied largely in isolation, to a more multifaceted holistic approach. DNA sequencing, structural variations mapping, CpG island methylation patterns, histone modifications, nucleosomal remodeling, microRNA function and transcription profiling have been viewed in a more systematic way. However, technologies examining each of above aspects of the molecular state of the cells are often isolated, tedious and incompatible, which severely complicates a system biology analysis that requires coherent experimental data results.

Single molecule level analysis of large intact native biological samples could provide the potential of studying genomic and epigenomic information of the target samples in true meaningful wholesome analytical way such as overlaying the sequence structural variations with aberrant methylation patterns, microRNA silencing sites and other functional molecular information. See, e.g., PCT patent application US2009/049244, the entirety of which is explicitly incorporated herein by reference. It would provide a very powerful tool in understanding the molecular functions of cell and diseases genesis mechanism in personalized medicine.

Genome segments with no or low density of sequence specific motifs, bioinformatically fragment a genome map at such regions. Systematic DNA fragmentations coming from DNA isolation and/or sequence specific labeling also produce a fragmented genome map at the DNA break sites. Plug lysis based DNA recovery protocols produce long DNA molecules that are randomly fragmented. However nick-based labeling produces DNA fragmentation at defined fragile sites. These fragile sites occur at nicks on opposite DNA strands separated by a distance of less than or equal to 2 kb, leading to a specifically fragmented genome map.

Labeling DNA at sequence specific motifs asymmetrically distributed throughout the genome, followed by high throughput linearization of DNA molecules to interrogate labeling patterns, enables alignment of hundreds of overlapping linear DNA molecules to obtain a representative genomic map, preserving long range contextual information. The size of a genome map contig, overlapping DNA molecules sharing a common labeling pattern, is dependent on the presence of enough random DNA fragments covering a contiguous genome region, with sufficient overlap between fragments such that any overlap window comprises a unique labeling pattern.

DNA Methyltransferases (MTases) modify nucleic acids in a sequence-specific manner without temporarily compromising stand integrity or strand phosphodiester bond integrity. DNA MTases naturally catalyze the methyl group transfer from the cofactor S-adenosyl methionine (SAM) onto nucleobases within double-stranded DNA. Furthermore, when supplied with a modified cofactor, such as a modified SAM, an MTase can tag DNA at a sequence specific site with a transferable tag from the modified cofactor rather than with a simple methyl group without damaging the DNA backbone.

Other means of sequence specific labeling without damaging or severing the DNA backbone comprise the use of triple helix oligonucleotide based probes, peptide nucleic acid based probes, linked nucleic acid based probes, polyamide based probes, a zinc finger DNA binding domain, a transcription activator like (TAL) effector DNA binding domain, a transcription factor DNA binding domain, an inactivated restriction enzyme, an antibody, a methyl-DNA binding moiety, a DNA binding protein, or any combination thereof modified to include a detectable tag as listed above.

When such labeled large genomic DNA is extended linearly on supporting surfaces or inside nanochannel arrays, the spatial distance between signals from decorated probes hybridized on the sequence specific flaps is consistently and quantitatively measurable and hence will generate unique "barcode" signature patterns reflecting specific genomic sequence information in that region. The methyltransferase-delivered polynucleic acid tags are suitably created by specific enzymes, including but not limited to M1.SapI/M2.SapI, M.EcaI/M.BstEII, RM.MaqI, RM.Sno506I, M.SmaI/M.Cfr9I/MCphBI/M.Pac25I/M.TspMI/M.XcyI/M.XmaI/M.XveII, M.KpnI, M.EcoRV, M.SpeI, M.NheI/M.BmtI, M.ApaLI, M.BsaHI/M.HgiDi/M.HgiGI/M.HindV, RM.RdeGBI, M.CpeAVI/M.BstZ17I, M.HpaI, M.BamHI, M.HincII and M.HindII, M.MspAlI, M.BbrUI/M.BloAI/M.KasI/*M.M1aZV/M.PluTI/M.SfoI, M.AclI, M.BssSI, M1.BsrBI/M2.BsrBI, M.BsaAI/*M.Ppu21I, RM.AspNLS2ORF1089P/RM.PspOMII, M.HaeII/M.NgoAI/M.NgoBI, RM.RflFIII, *M.Eco72I/M.PmlI, alone, in combination with at least one of one another, or in combination with or replaced by one or more unlisted methyltransferase enzymes consistent with the disclosure herein, and or optionally in combination with one or more enzymes or proteins involved in the nonspecific binding of a nucleic acid. Based on this map, sequencing can be performed or sequence information assembled to incorporate long-range structural information.

In some embodiments, individually labeled unfolded nucleic acid molecules are linearly extended by physically confining such elongated macromolecules within nanoscale channels, topological nanoscale grooves or nanoscale tracks defined by surface properties.

In some embodiments, extremely small nanofluidic structures, such as nanochannels, were fabricated on a surface and used as massively parallel arrays for the manipulation and analysis of biomolecules such as DNA and proteins at single molecule resolution. Preferably, the size of the cross sectional area of channels is on the order of the cross sectional area of elongated biomolecules, i.e., on the order of about 1 to about $10^6$ square nanometers, to provide elongated (e.g., linear, unfolded) biomolecules that can be individually isolated, yet analyzed simultaneously by the hundreds, thousands, or even millions. Likewise, it is also desirable that the length of the channels is long enough to accommodate a substantial portion of macromolecules, ranging from the length of single field of view of a typical CCDA camera with optical magnification (about 100 microns) to as long as an entire chromosome, which can be on the order of 10 centimeters long. In some embodiments, a single microfluidic ship having at least 100, at least 1,000, at least 5,000, at least 10,000 or more nanochannels may be used to the analysis a plurality of biomolecules, such as DNA molecules. It is appreciated that using such microfluidic chips enables the simultaneous analysis of a large number of molecules and leads to highly efficient assays. For example, a multiplexed assay may be completed in less than 2 hours, less than 1 hour, less than 30 minutes, less than 20 minutes, less than 10 minutes, less than 5 minutes, less than 1 minute, less than 30 seconds, less than 20 seconds, less than 10 seconds, less than 5 seconds, or less than 1 second.

The present disclosure also relates to the uses of such labeling processes and features, and to conditions for which the use of the techniques disclosed herein yields improved results. As discussed below, conditions needed for maximum contig, complex genome assembly include: motif(s) repeat density of 5-25 per 100 kb (best 7-15), Error rate ≤20%, Stretch factor >70% (ideal 80-85%), stretch variability <20%, and interrogation of molecules ≥150 kb, preferably ≥180 Kb. Preferably a plurality of molecules being analyzed are ≥150 kb or ≥180 kb, and most preferably the population of molecules being analyzed includes sufficient molecules of ≥150 kb, or advantageously ≥180 kb, to give at least 5×, 10×, 15×, 20×, 25×, 30×, 40×, 50×, 60×, 70×, 80×, 90×, or 100× or greater coverage of the genomic region being analyzed. In some embodiments, the genomic region being analyzed is, is at least, is about 500 kb, 800 kb, 1 Mb, 1.5 Mb, 2 Mb, 3 Mb, 4 Mb, 5 Mb, 7 Mb, 10 Mb, 15 Mb, 20 Mb, or a range between any two of the above values, where Mb refers to megabase sizes and kb refers to kilobase sizes.

In some embodiments, a complex color of spatial barcoding patterns of labeled DNA can be designed to interrogate multiple regions for multiplexed disease diagnostics. As one non-limiting example, the user could interrogate multiple regions for multiple translocations.

In some embodiments, a methyltransferase can be selected to target at least one variable length region on at least one specific chromosome. The presence of extra or less copies of that region can be used to diagnose an associated disease.

In some embodiments, the procedures are used to identify pathogen genomes, for example in a patient sample. A methyltransferase can be selected that produces a distinct bar code pattern in a host genome as compared to a pathogen genome. The presence of a pathogen-specific pattern may indicate the presence of the pathogen in host tissue.

Methyltransferase Enzymes.

Non-limiting exemplary Methyltransferase enzymes are discussed in, for example, U.S. Pat. No. 8,008,007, published Aug. 30, 2011, which is hereby expressly incorporated by reference in its entirety. Methyltransferase enzymes suitable for use in the methods, compositions and systems disclosed herein include, but are not limited to M.AacDam, M.AatII, M.AbaORFDP, M.AbaORFKP, M.AbrI, M.AbrI, M.AbrIII, M.AciI, M.AclI, M.AcuI, M.Afa22MI, M.AflII, M.AflIII, M.AgeI, M.AhdI, M.AhyBP, M.AlaK2I, M.AluI, M.AlwI, M.Alw26I, M.ApaI, M.ApaLI, M.ApeKI, M.ApoI, M.AquI, M.AscI, M.AseI, M.AseII, M.AsiSI, M.AspCNI, M.AtuCI, M.AtuCORF1997P, M.AtuDORF794P, M.AtuDORF3839P, M.AvaI, M.AvaII, M.AvaIII, M.AvaIVP, M.AvaV, M.AvaVI, M.AvaVII, M.AvaVIII, M.AvaIX, M.AvaORF3700P, M.AvaORF7270P, M.AvrI, M.AvrII, M.BabI, M.BaeI, M.BalI, M.BamHI, M.BamHII, M.BanI, M.BanII, M.BanIII, M.BatAORF3814P, M.BatA581ORF3846P, M.Bbu297I, M.BbvI, M1.BbvCI, M2.BbvCI, M.BbvSI, M1.BccI, M2.BccI, M.Bce1247I, M1.BceAI, M2.BceAI, M.Bce14579ORF939P, M.BceSORF365P, M.BceSORF4605P, M1.BceSORF5606P, M2.BceSORF5606P, M.Bcep1P, M.Bcep43ORFAP, M.BchI, M.BcII, M1.BcnI, M2.BcnI (M.BcnIB), M1.BcoKI, M2.BcoKI, M.Bcs139P, M.BdiI, M.BepI, M1.BfaI, M2.BfaI, M.BfaORFC157P, M2.BfiI (M.BfiC2), M1.BfuA1, M2.BfuAI, M.BgII, M.BgIII, M1.BhaI, M2.BhaI, M.BhaII, M.BjaORF2509P, M.BloNORF564P, M.BloNORF1473P, M.B1pI, M.BmaI, M.BmaPhiE125ORF56P, M.Bme216I, M.BmeLORF1444P, M.BmeTI, M1.BmrI, M2.BmrI, M.BnaI, M.BpmI, M1.Bpu10I, M2.Bpu10I, M1.BsaI, M2.BsaI, M.BsaAI, M.BsaJI, M.BsaWI, M1.BscGI, M2.BscGI, M.Bse634I, M.BseCI, M.BseDI, BseMII, BseRI, M.BseRI, M.BseYI, BsgI, M.BsgI, M.BsiWI, M.BslI, M1.BsmI, M2.BsmI, M.BsmAI, M.BsmBI, M.BsoBI, M.BspI, M.Bsp6I, M.Bsp50I, M.Bsp98I, M.Bsp106I, M.Bsp143II, BspCNI, M.BspCNI, M.BspEI, M.BspHI, M.Bsp1S4I, M.BspKT6I, BspLU11III, M1.BspLU11III, M2.BspLU11III, M1.BspMI, M2.BspMI, M.BspMII, M.BspRI, M.BspST5I, M1.BsrI, M2.BsrI, M1.BsrBI, M2.BsrBI, M.BsrFI, M.BssHI, M.BssHII, M.BssSI, M.BstI, M.BstEII, M.BstEIII, M1.BstF5I, M2.BstF5I, M3.BstF5I, M4.BstF5I, M.BstGII, M.BstLVI, M.BstNI, M.BstNBI, M.BstVI, M.BstXI, M.BstYI, M.Bsu15I, M.Bsu36I, M.Bsu6633I, M.BsuBI, M.BsuEII, M.BsuFI, M.Bsu1330ORF491P, M.BsuRI, M.BthIPS78, M.BthVORF4625P, M.BusLBORFC747P; M.BusLBORFC755P, M.Cac8I, M.Cac824I, M.Cac824ORF3358P, M.CauJORFC101P, M.CauJORFC102P, M.CauJORFC103P, M.CauJORFC104P, M.CauJORFC107P, M.CauJORFC110P, M.CauJORFC111P, M.CboI, M.CcrMI, M.Cdi630I, M.CdiCD6I, M.CdiCD6II, M.Cdi630ORF898P, M.CefORF1493P, M.CeqI, M.CfrI, M.Cfr6I, M.Cfr9I, M.Cfr10I, M.Cfr13I, M.Cfr42I, M.CfrAI, M.CfrBI, M.CggI, M.CglASI, M.CglILP6P, M.CjeNI, M.Cje81116ORFBP, M.Cje81116ORFCP, M.ClaI, M.Csp6I, M.Csp68KI, M.Csp68KIV, M.Csp68 KV, M.CteEORF387P, M.CthORFS26P, M.CthORFS34P, M.CthORFS93P, M.CviAI, M.CviAII, M.CviAIV, M.CviBI, M.CviBII, M.CviBIII, M.CviORF5P, M.CviORF2111P, M.CviPI, M.CviQI, M.CviQII, M.CviQIII, M.CviQIVP, M.CviQVP, M.CviQVI, M.CviQVII, M.CviQVIIIP, M.CviQIXP, M.CviQXP, M.CviQXI, M.CviRI, M.CviRII, M.CviSI, M.CviSII, M.CviSIII, M.CviSIVP, M.CviSVP, M.CviSVIP, M.CviTI, M.DdeI, DhaORFC135P, M1.DpnII, M2.DpnII, M.DraI, M.DraII, M.DraIII, M.DsaV, M.DvuORF19P, M.DvuORF2842P, M.EacI, M.EaeI, M.EagI, M1.EarI, M2.EarI, M.EcaI, M.Ec118kI, M1.Eco3I, M2.Eco3I, M.Eco32I, M.Eco47II, M.Eco47III, M.Eco56I, Eco57I, M.Eco57I, M.Eco64I, M.Eco72I, M.Eco88I, M.Eco98I, M.Eco105, M.Eco147I, M.Eco23I, M.Eco255I, M.Eco536P, M.Eco1639P, M.Eco183I, M.Eco248534P, M.EcoAI, M.EcoBI, M.EcoCFTDamP, M.EcoCFTDam2P, M.EcoCFTDam3P, M.EcoCFTDcmP, M.EcoDI, M.EcoDR2, M.EcoDR3, M.EcoDXXI, M.Eco67Dam, M.EcoEI, M.EcoHI, M.EcoHK31I, M.EcoKI, M.EcoKII, M.EcoKDam, M.EcoKDcm, M.EcoKO157DamP, M.EcoKO157Dam2P, M.EcoKO157Dam3P, M.EcoKO157DcmP, M.EcoKO157ORF1953P, M.EcoLahn1P, M.EcoLahn3P, M.EcoNI, M.EcoNi12P, M.EcoO109I, M.EcoO157DamP, M.EcoO157DcmP, M.EcoO157ORF1454P, M.EcoO157ORF2389P, M.EcoO157ORF3349P, M.Eco536ORF3P, M.EcoPI, M.EcoP15I, M.EcoPlDam, M.EcoPhi4795DamP, M.EcoRI, M.EcoRII, M.EcoRV, M.EcoR124I, M.EcoR124II, M.EcoRD2, M.EcoRD3, M.EcoStxlDamP, M.EcoStx2DamP, M.EcoT22I, M.EcoT38I, M.EcoT1Dam, M.EcoT2Dam, M.EcoT4Dam, M.EcoVIII, M.EcoVT2Dam, M.EcoWphiP, M.Eco29kI, M.EcopHSHP, M.EcopHSH2P, M.EcoprrI, M.EfaHGSORFHP, M.EphPI ORF1P, M.EsaBC1I, M.EsaBC3I, M.EsaBC4I, M.EsaBS1I, M.EsaBS9I, M.EsaDix1I, M.EsaDix2I, M.EsaDix3I, M.EsaDix4I, M.EsaDixSI, M.EsaDix6I, M.EsaDix7I, M.EsaLHCI, M.EsaLHCIII, M.EsaRM1P, M.EsaRM13P, M.EsaRM16P, M.EsaRM17P, M.EsaRM21P, M.EsaRM38P, M.EsaRM61P, M.EsaRM63P, M.EsaRM65P, M.EsaRM67P, M.EsaRM69P, M1.EsaS1I, M2.EsaS1I, M.EsaS3I, M.EsaS4I, M.EsaS6I, M.EsaS7I, M.EsaS8I, M.EsaSS2P, M.EsaSS5P, M.EsaSS12P, M.EsaSS13P, M.EsaSS15P, M.EsaSS16P, M.EsaSS18P, M.EsaSS19P, M.EsaSS22P, M.EsaSS30P, M.EsaSS31P, M.EsaSS35P, M.EsaSS36P, M.EsaS540P, M.EsaSS43P, M.EsaSS47P, M.EsaSS48P, M.EsaSS49P, M.EsaSS52P, M.EsaSS55P, M.EsaSS57P, M.EsaSS67P, M.EsaSS69P, M.EsaS570P, M.EsaSS71P, M.EsaSS72P, M.EsaSS73P, M.EsaSS74P, M.EsaSS75P, M.EsaSS76P, M.EsaSS79P, M.EsaSS81P, M.EsaSS83P, M.EsaSS87P, M.EsaSS88P, M.EsaS590P, M.EsaSS96P, M.EsaSS97P, M.EsaSS103P, M.EsaSS104P, M.EsaSS105P, M.EsaSS106P, M.EsaSS107P, M.EsaSS108P, M.EsaSS109P, M.EsaSS110P, M.EsaSS111P, M.EsaSS113P, M.EsaSS117P, M.EsaSS120P, M.EsaSS123P, M.EsaSS126P, M.EsaSS130P, M.EsaSS131P, M.EsaSS134P, M.EsaSS136P, M.EsaSS137P, M.EsaSS144P, M.EsaSS145P, M.EsaSS150P, M.EsaSS153P, M.EsaSS154P, M.EsaSS155P, M.EsaSS156P, M.EsaSS160P, M.EsaSS163P, M.EsaSS165P, M.EsaSS167P, M.EsaSS169P, M.EsaSS170P, M.EsaSS172P, M.EsaSS174P, M.EsaSS177P, M.EsaSS181P, M.EsaSS182P, M.EsaSS186P, M.EsaSS187P, M.EsaSS192P, M.EsaSS195P, M.EsaSS200P, M.EsaSS214P, M.EsaSS215P, M.EsaSS216P, M.EsaSS218P, M.EsaSS221P, M.EsaSS222P, M.EsaSS223P, M.EsaSS225P, M.EsaSS228P, M.EsaSS237P, M.EsaSS238P, M.EsaSS241P, M.EsaSS244P, M.EsaSS245P, M.EsaSS246P, M.EsaSS247P, M.EsaSS254P, M.EsaSS259P, M.EsaSS264P, M.EsaSS266P, M.EsaSS268P, M.EsaSS269P, M.EsaSS270P, M.EsaSS275P, M.EsaSS278P, M.EsaSS281P, M.EsaSS282P, M.EsaSS283P, M.EsaSS289P, M.EsaSS297P, M.EsaSS302P, M.EsaSS303P, M.EsaSS305P, M.EsaSS315P, M.EsaSS317P, M.EsaSS318P, M.EsaSS319P, M.EsaSS323P, M.EsaSS326P, M.EsaSS328P, M.EsaSS329P, M.EsaSS334P, M.EsaSS335P, M.EsaSS329P, M.EsaSS51DamP, M.EsaSS65DamP, M.EsaSS138DamP, M.EsaSS198DamP, M.Esp3I, M.Esp1396I, M.EspRB49DamP, M.FauI, M.FnuDI, M.FnuDII, M.FnuDIII, M.Fnu4HI, M.FnuVDamP, M.FokI, M.FseI, M.FspI, M.FssI, M.GmeORFC6P, M.GmeORFC16P, M.GsuI, M.GviDamP, M.H2I, M.HaeII, M.HaeIII, M.HapII, M.HduDamP, M1.HgaI, M2.HgaI, M.HgiAI, M.HgiBI, M.HgiCI, M.HgiCII, M.HgiDI, M.HgiDII, M.HgiEI, M.HgiGI, M.HhaI, M.HhaII, M.HheORF238P, M.HheORF1050P, M.HheORF1244P, M.HheORF1445P, M.Hin1II, M.HinB231ORFDP, M.HinHP1Dam, M.HinHP2Dam, M.HinPII, M.HincII, M.Hindl, M.HindIII, M.HindIII, M.HindV, M.HindDam, M.HinfI, M.HinfIII, M.HjaI, M.HpaI, M.HpaII, M1.HphI, M2.HphI, M.HpyI, M.Hpy8I, M.Hpy87AP, M.Hpy99I, M.Hpy99II, M.Hpy99III, M.Hpy99IV, M1.Hpy99V, M2.Hpy99VP, M.Hpy99VI, M.Hpy99VIII, M.Hpy99IX, M.Hpy99X, M.Hpy99XI, M.Hpy166IV, M.Hpy1781P, M.Hpy188I, M.Hpy188II, M.Hpy188III, M.Hpy788606P, M.Hpy788845P, M.Hpy788849P, M.Hpy789115P, M.Hpy789117P, M.Hpy789137P, M.Hpy789145P, M.Hpy790101P, M.Hpy959772P, M.HpyAI, M1.HpyAI1, M2.HpyAII, M.HpyAIII, M.HpyAIV, M.HpyAV, M1.HpyAVI, M2.HpyAVI, M.HpyAVII, M.HpyAVIII, M.HpyAIX, M.HpyAX, M.Hpy87AI, M.HpyAORF263P, M.HpyAORF369P, M.HpyAORF481P, M.HpyAORF483P, M1.HpyCII, M2.HpyCII, M.HpyCH4IV, M.HpyCH4V, M.HpyCR2ORF1P, M.HpyCR2ORF3P, M1.HpyCR4RM1P, M2.HpyCR4RM1P, M.HpyCR9RM1P, M.HpyCR9RM2P, M.HpyCR14RM1P, M.HpyCR14RM2P, M.HpyCR15RM2P, M.HpyCR16RM1P, M.HpyCR29RM1P, M.HpyCR29RM2P, M.HpyCR35RM1P, M.HpyCR35RM2P, M1.HpyCR38RM1P, M2.HpyCR38RM1P, M.HpyCR38RM2P, M.HpyF17I, M.Hpy99ORF430P, M.Hpy99ORF433P, M.Hpy99ORF846P, M.Hpy99ORF1012P, M.HspNORF1543P, M.KasI, M.KpnI, M.Kpn2I, M.KpnAI, M.KpnBI, M.Kpn19097DamP, M.Kpn19097Dam2P, M.Kpn19097ORFFP, M.Kpn2kI, M.Lci22RP, M.LinFORF11323P, M.LinFORF12222P, M.LinFORF12737P, M.LinLORF903P, M.LinLORF1547P, M.LinLORF2668P, M1.LlaA1, M2.L1aAI, M.L1aBI, M.L1aCI, M.L1aDI, M.L1aDII, M1.L1aDCHI, M2.L1aDCHI, M.L1aKR2I, M.LmoAP, M.LmoEORF470P, M.LmoFORF327P, M.Lmo19115ORF1P, M.Lsp1109I, M.MamI, M1.MboI, M2.MboI, M1.MboII, M2.MboII, M.Mca43617ORFAP, M.Mca43617ORFBP, M1.Mca43617ORFDP, M2.Mca43617ORFDP, M.Mca43617ORFJP, M.MfeI, M.MjaI, M.MjaII, M.MjaIII, M.MjaIVP, M.MjaV, M.MjaVI, M.MloORFmIr7520P, M.MluI, M.MlyI, M.MmaMORFC174P, M.MmaSORF735P, M.MmeI, M.MmeII, M.MmoORF950P, M.MmoORF3450P, M.Mmy1P, M.MmySCORF186P, M.MmySCORF216P, M.MmySCORF950P, M1.MnII, M2.MnII, M.MpeORF1230P, M1.MpeORF1780P, M2.MpeORF1780P, M.MpeORF4940P, M.MpeORF9800P, M.MpuCORF430P, M.MscI, M.MseI, M.MsmChe9cORF76P, M.MsmChe9cORF77P, M.MsmChe9cORF80P, M.MsmcdP, M.MsmomegaORF127P, M.MspI, M.MspAlI, M.MspSD10I, M.MthFI, M.MthTI, M.MthZI, M.MunI, M.MvaI, M.Mva12691, M.MwoI, M.NaeI, M.NarAORFC306P, M.NcoI, M.NdeI, M.NdeII, M.Ngo18785P, M.Ngo185840P, M.Ngo185841P, M.NgoAI, M.NgoAII, M.NgoAIII, M.NgoAIV, M.NgoAV, M.NgoAVIIP, M.NgoAXIP, M.NgoAORFC708P, M1.NgoAORFC717P, M2.NgoAORFC717P, M.NgoBI, M.NgoBII, M.NgoBIIIP, M.NgoBIVP, M.NgoBV, M1.NgoBVIII, M2.NgoBVIII, M.NgoBIX, M.NgoBXII, M.NgoDIII, M.NgoEI, M.NgoFVII, M.NgoGI, M.NgoGII, M.NgoGIII, M.NgoGIVP, M.NgoGV, M.NgoHIP, M.NgoHIIP, M.NgoHIIIP, M.NgoHIVP, M.NgoHVP, M.NgoHVIP; M.NgoHVIIP, M.NgoHVIII, M.NgoKVIP, M.NgoLIP, M.NgoLII, M.NgoLIIIP, M.NgoLIVP, M.NgoLVP, M.NgoMI, M.NgoMII, M.NgoMIII, M.NgoMIV, M.NgoMV, M.NgoMVIII, M.NgoMXV, M.NgoNIP, M.NgoNII, M.NgoNIIIP, M.NgoNIVP, M.NgoNVP, M.NgoPIP, M.NgoPII, M.NgoPIII, M.NgoPIVP, M.NgoPVP, M.NgoQIP, M.NgoQIIP, M.NgoQIIIP, M.NgoQIVP, M.NgoQVP, M.NgoSIP, M.NgoSII, M.NgoSIIIP, M.NgoSIVP, M.NgoSVP, M.NgoTIP, M.NgoTII, M.NgoTIIIP, M.NgoTIVP, M.NgoTVP, M.Ngo125VIIP, M.NlaI, M.NlaIII, M.N1aIV, M.N1aX, M.N1aL17ORFAP, M.NmaPhiCh1I, M.NmeAORF1453P, M.NmeAORF1500P, M1.NmeB1, M2.NmeBI, M.NmeBF13P, M.NmeBORF1033P, M.NmeBORF1290P, M.NmeSI, M.NmeST1117ORF1P, M.NmepNLE1P, M.NpuORFC221P, M.NpuORFC222P, M.NpuORFC224P, M.NpuORFC226P, M.NpuORFC228P, M.NpuORFC230P, M.NpuORFC231P, M.NpuORFC234P, M.NsiI, M.NspI, M.NspIII, M.NspV, M.NspHI, M.OihORF3333P, M.OihORF3336P, M.OkrAI, M.Pac25I, M.PaeI, M.Pae1MORF3201P, M.PaeMSHORF1P, M.Pae2164ORF7P, M.PaeR7I, M.PfIMI, M.PgiI, M.PhaI, M.PhiBssHII, M.PhiMx8I, M.Phi3TI, M.Phi3TII, M.PhoI, M.PhoII, M.PhoWORFBP, M.PhsOYDam1 P, M.PhsOYDam2P, M.PhsOYDam3P, M.PhsOYDam4P, M.PhsOYDam5P, M.PleI, M.PleLFBORF8P, M.P1uTDamP, M.P1uTDcmP, M.P1uTORF600P, M.P1uTORF2710P, M.PluTORF2942P, M.Pmi16525DamP, M.Pmi1 6525Dam2P, M.Pmi16525ORFDP, M.PmuADam, M.PmuDam, M.Ppu21I, M.Ppu111I, M.Ppu1253I, M.PpuMI, M.PshAI, M.PspGI, M.PspPI, M.PstI, M.PvuI, M.PvuII, M.PvuRts1DamP, M.PvuRts1Dam2P, M.RcoORF690P, M.ReuORF325P, M.Rho11sI, M.Rho11sII, M.R1e39BI, M.RmeADam, M.RpaORF1026P, M.RpapRPA4P, M.Rrh4273I, M.RruMORFS5P, M.RruMORFS15P, M.RsaI, M.RshI, M.RshIII, M.RsrI, M.RsrII, M.SPBetaI, M.SsrII, M.SacI, M.SacII, M.SalI, M2.SapI, M.Sau961, M.Sau32391, M.Sau67821, M.Sau3AI, M.SauLPI, M.SbaI, M.SbfI, M.Sbo13I, M.ScaI, M1.5crF1, M2.5crFI, M.SduI, M.SenPI, M.SenPhiE15P, M.SenPhiE15DamP, M.SenpCI, M.SeqORFC57P, M.SeqORFC272P, M.SeqORFC448P, M.SfaNI, M.SfeI, M.SfiI, M.Sfl2DamP, M.Sfl2DcmP, M.Sfl2ORF3300P, M.SflSf6DamP, M.SflTDamP, M.SflTDcmP, M.SflTORF3517P, M.Sfl2a1, M.SfoI, M.Sho27844P, M.SinI, M.SmaI, M.SmaII, M.SmapR478DcmP, M.SmapR478ORF272P, M.Sme1P, M1. SmuUORF504P, M2.5muUORF504P, M.SnaBI, M.SonDamP, M.SonORF4P, M.SpeI, M.SphI, M.Spn526P, M.Spn6BI, M1.Spn19FORF24P, M2.Spn19FORF24P, M.Spn19FORF927P, M.SpnHGORF4P, M.SpnORF 1431 P, M.SpnORF 1849P, M.SpnRORF 1287P, M.SpomI, M.SptAI, M.SscL1I, M.Sse9I, M.SsIII, M.SsoI, M.SsoII, M.Ssp68031, M.Ssp6803ORF729P, M.Ssp6803ORF1803P, M.SspPhiBt1 P, M.SssI, M.SstI, M.Ssu211I, M.Ssu2121, M1.Ssu24791, M2.5su24791, M1 Ssu41091, M2.5su41091, M1.Ssu49611, M2.5su49611, M1 Ssu80741, M2.5su80741, M1.Ssu11318I, M2.5su11318I, M1.SsuDAT1I, M2.5suDAT1I, M.Sth368I, M.SthSt81P, M.StsI, M.StyI, M.StyCDamP, M.StyCDam2P, M.StyCDam3P, M.StyCDam4P, M.StyCDcmP, M.StyD4I, M.StyDam, M.StyDam2P, M.StyDam3P, M.Sty1344Dam, M.Sty14028Dam, M.StyHCM1ORF187P, M.StyLTI, M.StyLTIII, M.StyLT2Dam, M.StyLT2DcmP, M.StyLT2FelsDamP, M.StyR27ORF154P, M.StySPI, M.StySKI, M.StySPI, M. StySQI, M.StySopEDamP, M.StyTDamP, M.StyTDam2P, M.StyTDam3P, M.StyTDam4P, M.StyTDcmP, M.SuaI, M.TaeII, M.TaqI, M.TdeII, M.TdeIII, M.TdeORF706P, M.TelBORF1578P, M.TelBORF1640P, M.TelBORF1878P, M1.TerORFS1P, M2.TerORFS1P, M.TerORFS14P, M.TerORF518P, M.TerORFS62P, M.TerORF5122P, M.TfiTok6A1I, M. ThaI, M. ThaII, M. ThaIII, M.TliI, M.TmaI, M.TpaI, M.TrsKTI, M.TrsSI, M.TrsTI, M.TseI, M.Tsp32I, M.Tsp45I, M.Tsp509I, M.TspRI, M.Tth111I, Tth111II, M.TthHB81, M.TthHB27P, M.TthHB27ORF41P, M.TvoORF849P, M.TvoORF1192P, M.TvoORF1400P, M.TvoORF1413P, M.TvoORF1416P, M.TwhORF771P, M.TwhTORF783P, M.Uba580P, M.Ucrl P, M.Van91II, M.VchADamP, M.Vch569BdamP, M.VchO395Dam, M.VchK139I, M.VpaRDamP, M.VspI, M.VvuDamP, M.VvuYDamP, M.WsuORF1405P, M.WsuORF1930P, M.XamI, M.XaxCORF2436P, M.XbaI, M.XcmI, M.XcyI, M.XfaAORFC345P, M.XfaAORFC348P, M.XfaOORFC725P, M.XfaORF1804P, M.XfaTORF577P, M.XfaTORF1062P, M.XfaTORF1607P, M.XhoI, M.XhoI, M.XmaI, M.XmaIII, M.XmnI, M.XorII, M.XphI, M.YenI, M.YenSDamP, M.YenSORFC666P, M.YenWI, M.YpeDamP, M.YpeKDamP, M.YpeKORF2224P, M.YpeKORF3792P, M.YpeMDamP, M.YpeMORF1932P, M.YpeMORF3790P, M.YpeORF391P, M.YpeORF2088P, and M.YpsDam. Additional or alternate methyltransferase enzymes are also contemplated herein.

A list of preferred methyltransferases (isoschizomers shall be included as well) consistent with the disclosure herein includes the following.

TABLE 1

MTases from REBASE for labeling human genome

| Methyltransferase | Recognition sequence | Base | Sites/100 kb |
|---|---|---|---|
| M.XorII | CGATCG | C5 | 0.4 |
| M.SalI | GTCGAC | N6A | 1 |
| M.XamI | GTCGAC | NN | 1 |
| M.AgeI | ACCGGT | C5 | 1.7 |
| M.BanIII | ATCGAT | NN | 2.8 |
| M.BsecI | ATCGAT | N6A | 3 |
| M.NspV | TTCGAA | NN | 3.4 |
| M.Xho | CTCGAG | N6A | 3.9 |
| M.AbrI | CTCGAG | NN | 3.9 |
| M.BstVI | CTCGAG | N6A | 3.9 |
| M.PaeR7I | CTCGAG | N6A | 3.9 |
| RM.MaqI | CRTTGAC | N6A | 9 |
| M.NheI | GCTAGC | NN | 9.1 |
| M.KpnI | GGTACC | N6A | 9.3 |
| RM.RdeGBI | TGRYCA | N6A | 10 |
| M.AvaIX | RCCGGY | C5 | 10.5 |
| RM.Cgl13032I | ACGABGG | N6A | 10.8 |
| M.EcaI | GGTNACC | N6A | 10.8 |
| RM.Sno506I | GGCCGAG | N6A | 11.2 |
| M.BamHI | GGATCC | N4C | 11.7 |
| M.SmaI | CCCGGG | N4C | 12.1 |
| M1/M2.BspQI | GCTCTTC | N4C? | 12.1 |
| M.XcyI | CCCGGG | NC4 | 12.1 |
| M.HpaI | GTTAAC | N6A | 12.5 |
| M.BssSI | CACGAG | N4C | 12.5 |
| RM.AspNLS2ORF1089P | CGCCCAR | N6A | 13 |
| M.SpeI | ACTAGT | NN | 13.5 |
| M.BstZ17I | GTATAC | NN | 13.7 |
| M.BstZ17I | GTATAC | NN | 13.7 |
| M.CpeAVI | GTATAC | N6A | 13.7 |
| M.TcoKWC4I | GTATAC | N6A | 13.7 |
| RM.Hpy26695ORFAP | GCGTA | N6A | 13.8 |
| M.EcoRV | GATATC | N6A | 13.9 |
| M.CeqI | GATATC | N6A | 13.9 |
| M.Mva1261II | GATATC | N6A | 13.9 |
| M.BsaHI | GRCGYC | C5 | 14.8 |
| M.ApaI | GGGCCC | C5 | 14.8 |
| RM.Cdi241ORF1691P | GCGGAG | N6A | 14.9 |
| M.ApaLI | GTGCAC | C5 | 15.9 |
| M.ScaI | AGTACT | N4C | 17.4 |
| M.SphI | GCATGC | NN | 17.6 |
| M.MfeI | CAATTG | N6A | 17.7 |
| M.MunI | CAATTG | N6A | 17.7 |
| M.HaeII | RGCGCY | C5 | 17.8 |
| M1.HgaI | GACGC | C5 | 18.1 |
| M1.Zfo19928ORFVP | GGCGGA | C5 | 18.3 |
| M.XorPXORF3955P | CCGAGG | N6A | 18.7 |
| M.AvrII | CCTAGG | NN | 19.1 |
| M.CthBORF256P | CCTAGG | NN | 19.1 |
| M.SacI | GAGCTC | C5 | 19.2 |
| RM.HauORF1937P | GGCCAAG | N6A | 19.3 |
| M.AflIII | CTTAAG | NN | 20.7 |
| M.Esp3I | CGTCTC | C5N6A | 20.7 |
| M.AflIII | CTTAAG | NN | 20.7 |
| M.AplAORF370P | CTTAAG | NN | 20.7 |
| M.LmoH7I | GTATCC | NN | 22.1 |
| M.LmoJ1816I | GTATCC | N6A | 22.1 |
| M.BsaAI | YACGTR | C5 | 22.4 |
| M1.BceAI | ACGGC | N4C | 22.4 |
| M.HindVI | CGAAT | N6A | 23.1 |
| M.FnuDII | CGCG | C5 | 23.4 |
| M.BclI | TGATCA | N6A | 23.6 |

TABLE 1-continued

MTases from REBASE for labeling human genome

| Methyltransferase | Recognition sequence | Base | Sites/100 kb |
|---|---|---|---|
| M.NcoI | CCATGG | N4C | 24.3 |
| M.BglII | AGATCT | N4C | 24.9 |
| M.EcoRI | GAATTC | N6A | 25.2 |
| RM.Nme2594ORF104P | GCCGAG | N6A | 25.2 |
| M.RsrI | GAATTC | N6A | 25.2 |
| M.SsoI | GAATTC | N6A | 25.2 |
| M.Cdi630III | CCSSGG | NC4 | 25.7 |
| M.XbaI | TCTAGA | N6A | 25.8 |
| M.StuI | AGGCCT | NN | 25.9 |
| M.Eco1524I | AGGCCT | NN | 25.9 |
| M.BceSI | CGAAG | N6A | 26.2 |
| M.HindIII | AAGCTT | N6A | 27.1 |
| M.BsrGI | TGTACA | NN | 27.3 |
| RM.AbaCIII | CTATCAV | | 27.7 |
| RM.EsaS13ORFC1P | GACCAC | N6A | 28.6 |
| M.NdeI | CATATG | N6A | 29 |
| M.AspCNI | GCSGC | C5 | 29 |
| M.BfaSIII | ATGCAT | N6A | 29.8 |
| M.BspHI | TCATGA | N6A | 31.3 |
| M.PvuII | CAGCTG | NC4 | 34.7 |
| M.BsuBI | CTGCAG | N6A | 41.9 |
| M.BsuBI | CTGCAG | N6A | 46.9 |
| M.RpaII | CTGCAG | N6A | 46.9 |
| M.BbrUIII | CTGCAG | N6A | 46.9 |
| M.AseI | ATTAAT | N6A | 48 |
| M. VspI | ATTAAT | N6A | 48 |
| M.Eco57IB | CTGAAG | N6A | 69.3 |
| M.FokI | GGATG | N6A | 165.7 |
| M.BbvI | GCAGC | C5 | 168 |
| M.MboIIA | GAAGA | N6A | 283.9 |

REBASE Recognition sequences representations use the standard abbreviations (Eur. J. Biochem. 150: 1-5, 1985) to represent ambiguity: R = G or A; Y = C or T; M = A or C; K = G or T; S = G or C; W = A or T; B = not A (C or G or T); D = not C (A or G or T); H = not G (A or C or T); V = not T (A or C or G); N = A or C or G or T.
These are written from 5' to 3', when only one strand is shown.

Methyltransferase enzymes may be used without modification or may be optimized to increase the efficiency of transfer of one or more cofactors or modified cofactors to a nucleic acid substrate. Modifications to increase the efficiency of transfer of one or more cofactors or modified cofactors to a nucleic acid substrate are discussed in, for example, Lukinavicius et al. (2007) "Targeted Labeling of DNA by Methyltransferase-Directed Transfer of Activated Groups (mTAG)" J. Am Chem. Soc. 129:2758-2759, published Feb. 27, 2007, which is hereby explicitly incorporated by reference in its entirety, or Lukinavicius et al., (2012) "Engineering the DNA cytosine-5 methyltransferase reaction for sequence-specific labeling of DNA" Nucleic Acid Research 40(22):11594-11602, published Oct. 5, 2012, which is hereby explicitly incorporated by reference in its entirety. Briefly, in one approach, homology-based engineering may be used to identify residues such as those which correspond to Glutamine 82 of Motif IV and to Asparagine 304 of Motif X of Bacterial M.HhaI. Mutations may be introduced that mimic a Q82A or an N304A or both a Q82A and an N304A in a methyltransferase having homology in Motifs IV and X to M.HhaI, which are demonstrated to increase transfer of labels to target DNA.

Other mutations and other approaches for increasing methyltransferase labeling of substrate DNA with a conjugate are contemplated herein and are consistent with the methods, devices and compositions disclosed herein.

Methyltransferase Labeling Methods.

Nucleic acids may be labeled sequence-specifically using a number of methyltransferase labeling methods consistent with the disclosure herein. One set of methods of labeling, Sequence-specific Methyltransferase-Induced Labeling (SMILing), involves coupling whole modified cofactor molecules such as aziridine or N-mustard to target DNA sequence. SMILing labeling techniques are described in, for example, Pljevaljcic, G., Schmidt, F. and Weinhold, E. (2004) Sequence-specific methyltransferase-induced labeling of DNA (SMILing DNA). Chembiochem, 5, 265-269, which is hereby explicitly incorporated by reference in its entirety, and in Comstock, L. R. and Raj ski, S. R. (2005) Conversion of DNA methyltransferases into azidonucleosidyl transferases via synthetic cofactors. Nucleic Acids Res., 33, 1644-1652, which is hereby explicitly incorporated by reference in its entirety. Other SMILing cofactors and techniques consistent with the disclosure herein are contemplated.

A second exemplary set of methods of sequence-specific DNA labeling involves modified cofactors with activated sulfonium-bound side chains. These methods (named methyltransferase-directed Transfer of Activated Groups, mTAG) permit targeted transfer of these linear side chains alone. mTAG labeling techniques are described in, for example, Dalhoff, C., Lukinavicius, G., Klimasauskas, S. and Weinhold, E. (2006) Direct transfer of extended groups from synthetic cofactors by DNA methyltransferases. Nat. Chem. Biol., 2, 31-32 which is hereby explicitly incorporated by reference in its entirety, and in Lukinavicius, G., Lapiene, V., Stasevskij, Z., Dalhoff, C., Weinhold, E. and Klimasauskas, S. (2007) Targeted labeling of DNA by methyltransferase-directed transfer of activated groups (mTAG). J. Am. Chem. Soc., 129, 2758-2759, which is hereby explicitly incorporated by reference in its entirety.

Nick-Labeling.

As an alternative in some embodiments, nick labeling may be used to sequence-specifically label target DNA molecules. Methods of nick labeling in the context of the disclosure herein are found in references previously discussed herein and, for example, in U.S. Pat. No. 7,960,105, issued Jun. 14, 2011, which is hereby explicitly incorporated by reference in its entirety.

Modified Cofactors.

A number of modified cofactors are consistent with the methods, compositions and apparatuses disclosed herein. The term "modified cofactor" or "synthetic cofactor" used herein refer to a molecule that is different from the natural cofactor of DNA MTases, SAM, but can function as a cofactor by a DNA MTase to label a DNA molecule in a sequence-specific manner. As disclosed herein, modified cofactors may be derived from the natural cofactor, SAM, by modifying the amino acid side chain. In some embodiments, a modified cofactor may be used to label a DNA molecule in a sequence-specific matter, for example, by labeling the DNA molecule with a transferable tag. In some embodiments, the whole modified cofactor may function as a transferable tag. A transferable tag may be detectable and function as a detectable tag, or alternatively, a transferable tag may find to a detectable tag, which is detectable. A variety of transferable tags or detectable tags may be contemplated, for example, a fluorophore, a quantum dot, a dendrimer, a nanowire, a bead, a hapten, streptavidin, avidin, neutravidin, biotin, a stabilized reactive group a radiolabel, an electromagnetic label, an azide, Dibenzocyclooctyne (DBCO), an alkyne, or a combination thereof. One may, for example, employ aziridine or N-mustard compounds as disclosed above, such as in the context of SMILing methyltransferase labeling discussed herein. One may employ sulfonium-bound side chains, such as in the context of mTAG labeling techniques discussed herein. In some embodiments a click label may be used. In some embodiments a transferable tag such an azide, Dibenzocyclooctyne (DBCO), or an alkyne may be used.

Transferable tags or detectable tags may be detected in a number of ways. For example, a transferable tag or detectable tag may be detected optically, such as fluorescent or chemical staining, electronically, electrically, electromagnetically, or a combination thereof. In some embodiments, transferable tags comprising a fluorophore are contemplated. Such transferable tags or detectable tags may be detected by subjecting labeled nucleic acid molecules to visible or infrared light at an excitation wavelength, such that the transferable tag or detectable tag absorbs and reemits the light energy, for example at a greater wavelength, such that the reemitted light may be detected as distinct from the excitation light energy.

Non-fluorescent transferable tags or detectable tags are also contemplated. Non-fluorescent transferable tags or detectable tags may rely upon a mechanism other that reemission of excitation energy in order to be detected as nucleic acid labels. For example, transferable tags or detectable tags may comprise a radiolabel that emits at least one alpha or beta particle as a means of detection. A transferable tag or detectable tags may comprise an epitope or other binding structure that may be conjugated to a receptor molecule to facilitate detection. In some embodiments, a transferable tag or detectable tag may comprise a member of a binding pair, for example, biotin and streptavidin, which may be detected using the other member of the binding pair.

Additional transferable tags or detectable tags are contemplated. For example, a transferable tag or detectable tag may comprise a chemical moiety having distinct charge or conductance properties, such that when passed through a current such as an electromagnetic current, optionally an electromagnetic current approximately perpendicular or perpendicular to the direction of passage of the nucleic acid through the detection device, the molecule or cofactor perturbs the current, by for example effecting a current blockade or perturbing the conductive properties of a conducting medium, such that the current is predictably altered in a manner such that the presence of the label may be detected.

Nonspecific Nucleic Acid Molecule Labels.

In some embodiments, only sequence-specific labels are used for generating maps of a genomic region from a nucleic acid sample. In some embodiments disclosed herein, sequence-specific labels or labeling cofactors are used in concert with nonspecific nucleic acid labels. Nonspecific labels bind a nucleic acid such as DNA or RNA in a manner that is independent of nucleic acid sequence. For example, some nonspecific labels may bind A:T base pairs generally, or G:C base pairs generally, or methylated bases generally (such as methyl-Cytosine) throughout a sample.

Examples of nonspecific DNA labels include Ethidium Bromide, which intercalates between Adenine-Thymidine base pairs in double-stranded DNA molecules in a manner that is largely independent of the specific nucleic acid sequence and which fluoresces in response to excitation by ultraviolet light. A SYBR dye such as SYBR® Green (N',N'-dimethyl-N-[4-[(E)-(3-methyl-1,3-benzothiazol-2-ylidene)methyl]-1-phenylquinolin-1-ium-2-yl]-N-propyl-propane-1,3-diamine) or a related SYBR dye having a different spectrum is a second example of a nonspecific DNA binding nonspecific label. In some embodiments a YOYO cofactor such as YOYO-1 Iodide may be used. In some embodiments a YOYO dye such as {1,1'-(4,4,8,8-tetramethyl-4,8-diazaundecamethylene)bis[4-[(3-methyl-benzo-1,3-oxazol-2-yl)methylidene]-1,4-dihydroquino-linium] tetraiodide}; a TOTO dye such as Quinolinium, 1-1'-[1,3-propanediylbis[(dimethyliminio)-3,1-propanediyl]]bis[4-[(3-methyl-2(3H)-benzothiazolylidene)methyl]]-, tetraiodide; a BOBO dye such as (1,1'-(4,4,7,7-tetramethyl-4,7-diazaundecamethylene)-bis-4-[(3-methyl-2,3-dihydro-(benzo-1,3-thiazole)-2-methylidene]-pyridinium tetraiodide); SYTO dye or SYPRO dye or a related nonspecific nucleic acid dye such as a DNA dye or a double-stranded DNA dye or label may be used. In some embodiments a POPO™ dye such as Benzoxazolium, 2,2'-[1,3-propanediylbis[(dimethyliminio)-3,1-propanediyl-1(4H)-pyridinyl-4-ylidenemethylidyne]]bis[3-methyl]-, tetraiodide or Benzoxazolium, 2,2'-[1,3-propanediylbis[(dimethyliminio)-3,1-propanediyl-1(4H)-pyridinyl-4-ylidene-1-propen-1-yl-3-ylidene]]bis[3-methyl]-, tetraiodide may be used. In some embodiments a Hoechst dye may be used. Additional nonspecific fluorescent DNA labels are contemplated.

Non-fluorescent nucleic acid labels are also contemplated herein. Examples of non-fluorescent nucleic acid labels include radiolabels such as $^{32}P$, $^{33}P$ or other radioactive nucleic which may be incorporated into or affixed to a nucleic acid molecule.

Radiolabeling, fluorescent labeling or other nonspecific nucleic acid labeling may be effected by incorporating the label into the molecule (for example as alpha-radiolabeled nucleotides), by selectively end-labeling the nucleic acid molecule (for example, using gamma-radiolabeled nucleotides), by intercalating the label into the nucleic acid molecule, by conjugating the label to a nonspecific single- or double-stranded nucleic acid binding protein or to a nucleic acid 5' or 3' end binding protein or to a blunt end binding protein, for example.

Nonspecific labels which delineate the total length of the labeled molecule are contemplated. In some embodiments nonspecific labels may bind to or otherwise associate with double-stranded DNA molecules independent of base identity. Examples of classes of molecules which may nonspecifically bind DNA include molecules which bind to the phosphodiester backbone or which bind to the major or minor groove of the double-helix in a sequence-independent manner. Fluorescently labeled or fluorescent DNA-binding polypeptides alone or comprising an in frame fusion to a fluorescent polypeptide such as GFP, as well as small molecule fluorescent labels such as SYBR® Green, Ethidium Bromide or DAPI (2-(4-amidinophenyl)-1H-indole-6-carboxamidine), as a non-limiting list of examples.

Nonspecific labels which delineate the total length of the labeled molecule may act by binding double-stranded DNA ends, DNA 5' phosphor, DNA 5' OH, DNA 3' phosphor, or DNA 3' OH groups, or by otherwise binding double-stranded DNA ends. Examples of DNA-break binding molecules include Rad52 proteins, Rap1p proteins or Ku proteins, any of which may, for example, be fused in frame to a fluorescent molecule such as GFP or otherwise bound to a fluorophore molecule, or may be labeled with a nonfluorescent marker such as a radiolabel.

In some embodiments, at least one nonspecific DNA label or at least one DNA end-label is used to delineate the length of a DNA fragment for which a DNA sequence-specific label has also been applied, such that information regarding both overall molecule length and the presence or absence of one or more repeats of one or more sequence specific motifs may be determined.

Comparison of Labeled Nucleic Acid Samples to Reference Sequences or Samples.

Samples comprising at least one labeled molecule as disclosed herein may be visualized as disclosed herein or previously, for example in references mentioned above and incorporated explicitly by reference in their respective entireties. Molecule visualization will generate a number of types of data that may be of use in comparing a visualized molecule to a reference or comparative sample.

Through the nonspecific double-stranded nucleic acid label or the nonspecific double-strand break label or other end label, one may determine the overall length of the nucleic acid molecule. Depending on how the fragment to be analyzed was generated, the length of the molecule may on its own provide sufficient information for mapping purposes, for example if a specific restriction endonuclease digest regime results in a unique fragment length in a specific sample type (a rearranged oncogene locus, or a fragment length that is unique to a pathogen genome and absent from an uninfected host, for example).

Thus in some embodiments an accurate measurement of labeled molecule length, in comparison with a control sample molecule of similar length or in comparison with a control sample that lacks a molecule of such length, or in comparison with genomic information from which a comparable 'digest' may be performed in silico to predict fragment lengths to which a sample may be compared, may lead to useful information or even a determination of sample identity or of the presence of a given allele or pathogen, for example, in a sample.

In many embodiments, identification of sample nucleic acids may require additional information, due perhaps to an inability to resolve minor differences in fragment length or due to the sample being nonspecifically fragmented into segments of suitable length. Accordingly, sequence-specific information may be obtained, for example using sequence-specific nucleic acid labeling as disclosed herein.

A number of reference genome types are contemplated herein. A reference genome may comprise a fully completed genomic sequence or may comprise a less than complete genomic sequence, such as a sequence harboring at least one gap, or a sequence of all or part of a single chromosome, BAC (bacterial artificial chromosome), YAC (yeast artificial chromosome) or contig.

A reference genome may comprise a consensus sequence for a species or population, single haplotype of a genomic sequence, a single haploid sequence, a full (largely duplicate) diploid genomic sequence or other subset of genomic sequence. A reference genomic sequence may reflect the genomic information from a 'wild-type' cell source or from a cell source harboring one or more mutations with respect to other cells in a given individual, such as mutations that may be associated with dysregulation of cell growth or division, such as one or more mutation associated with one or more types of cancer. A reference genome may be representative of a genome associated with one or more tumor cells. A reference genome may harbor at least one duplication, deletion, translocation, rearrangement or other structural variation as compared to a 'wild-type', healthy or consensus sequence.

A reference genome may comprise sequence information that is stored digitally and which is compared to a sample to be assayed through in silico computation-based analysis of a sample such as a labeled sample as compared to the reference genome. Alternately or in combination, a reference genome may comprise a second sample which is similarly treated and labeled, and for which fragment location and sequence position information is obtained. That is, a sample may be compared to a reference genome through in silico analysis or by directly comparing the information obtained to information obtained from a reference genomic sample, or by a combination of both in silico analysis and direct analysis.

A reference nucleic acid sample may originate from the same individual as does the sample to be assayed, from a separate individual of the same species, from a separate individual of a different species. A reference sample or reference genomic sequence may be used to compare normal vs. disease state, one disease state to another, treated vs. untreated or differentially treated, mutagenized vs. unmutagenized or differentially mutagenized, transformed vs. untransformed or differentially transformed, or other relative states of a pair of nucleic acid samples or a sample and a reference sequence.

Assembly of Fragments into Contigs and Whole Genome Maps.

Fragments may be assembled into contigs up to and including whole genome maps by a number of techniques such as those indicated below and throughout the present disclosure.

Assembler:

The assembler algorithm adopted the common Overlap-Layout-Consensus-Refinement schema, as described in multiple references, such as Anton Valouev, David C. Schwartz, Shiguo Zhou, and Michael S. Waterman, "An algorithm for assembly of ordered restriction maps from single DNA molecules" Proc Natl Acad Sci USA. 2006 Oct. 24; 103(43): 15770-15775, which is hereby explicitly incorporated by reference in its entirety, and Roy Ronen, Christina Boucher, Hamidreza Chitsaz, Pavel Pevzner, "SEQuel: improving the accuracy of genome assemblies" Bioinformatics. 2012 Jun. 15; 28(12): i188-i196, which is hereby explicitly incorporated by reference in its entirety. The Assembler starts with a list of all pair wise alignments that score above a specified P-Value threshold. This list is used to generate an overlap graph, which has maps as nodes and edges representing overlap between maps. A number of graph operations are used to remove redundant edges and spurious edges (False Positives). The resulting simplified graph should consist of a linear chain of overlapped maps for each contig. In practice the simplified graph still contains some spurious edges. In addition any repeats/duplications in the genome will result in alternate possible paths in the graph, even in the absence of spurious edges. The current algorithm outputs the longest path (layout) in the graph which has the specified minimum redundancy, length and coverage, removes the edges of this path from the graph and repeats until no more such paths are found. Each path found corresponds to a contig which is output along with the maps and their locations in the contig. If the genome had repeats/duplications, the resulting contigs may be incorrect, since only the first possible Assembly is output, but this happens relatively rarely since only repeats larger than the typical Molecule size will cause a problem. A draft quality map of each contig is computed by simple averaging of the overlapped regions of the map. The draft quality contig map has many small local errors that are subsequently corrected by refining the contig map by finding the maximum likelihood consensus map given the individual Molecule maps and their approximate locations in the contig. Alternate assembly techniques, such as those disclosed or contemplated in the literature may also be consistent with the disclosure herein (for example, Schatz et al., "The DNA60IFX contest" Genome Biology 2013, 14:124, which is hereby explicitly incorporated by reference in its entirety).

Refinement:

A program called RefAligner (available, for example, at http://bowtie.sourcearchive.com/documentation/0.12.71/classRefAligner_acd0f278c53bfbfdf3c63e2f6f4acde87.html and hereby explicitly incorporated by reference in its entirety) may be used to further improve the quality of each contig consensus map by finding additional Molecule maps from the complete set of Molecules that align with the contig. This larger set of maps is used to repeat the maximum likelihood optimization of each contig map. In addition the coverage of maps for each contig is analyzed to find lower coverage regions that may indicate that the contig is incorrectly joining two regions of the genome. If so, the contig is broken apart at the low coverage point. Alternate refinement techniques, such as those disclosed or contemplated in the literature may also be consistent with the disclosure herein.

Contig Extension:

After the initial Assembly and Contig Refinement, RefAligner or alternate software may be used to extend contigs. This is similar to Contig Refinement, except that after finding the Molecules that align with the contig, the consensus map is extended at each end as far as any single Molecule extends. The extension regions of the consensus map are initialized to have no sites. Then maximum likelihood optimization is used for the entire contig map to locate the sites in the extension region of the contig map. Finally the contig map is trimmed on both ends to remove regions with coverage below 3 (user adjustable).

Contig Merging:

Every pair of extended contig maps are aligned with each other (in both orientations) using a fairly stringent P-Value. Any contig pairs that align are merged together into a single contig. Contig Extension and Merging can be repeated several times until no further progress can be made.

Parameters for Improved Assembly Results.

It is disclosed herein that substantially improved alignment of a labeled nucleic acid molecule with a reference molecule, a reference dataset, or a second labeled nucleic acid molecule such as that necessary to assemble a population of labeled molecules into at least one contig, may be effected through use of at least one, two, three, four or all of the parameters disclosed herein. Conditions which it is disclosed herein to convey improved characteristics on the labeling and comparison methods and compositions disclosed herein include at least one of: motif(s) repeat density of 5-35 per 100 kb, such as 5-25 per 100 kb, Error rate ≤20%, Stretch factor >70%, stretch variability <20%, and interrogation of molecules >150 kb. Conditions which it is disclosed herein to convey further improved characteristics on the labeling and comparison methods and compositions disclosed herein include at least one of: motif(s) repeat density of 7-15 per 100 kb, stretch factor of 80-85%, and molecule size of greater than 180 kb.

That is, disclosed herein are beneficial effects of selecting motifs having a mean repeat density that is, is about, is less than, is greater than, 5, 6, 7, 8, 9, 10, 11, 12, 13, 14, 15, 16, 17, 18, 19, 20, 21, 22, 23, 24, or 25, or a range between any two of the above values, times per 100 kb, or any non-integer value within the aforementioned range. Disclosed herein are further beneficial effects of selecting motifs having a mean repeat density that is, is about, is less than, is greater than, 7, 8, 9, 10, 11, 12, 13, 14, or 15, or a range between any two of the above values, times per 100 kb, or any non-integer value within the aforementioned range. Disclosed herein are beneficial effects of maintaining an error rate that is, is about, is less than, is greater than, 0, 1%, 2%, 3%, 4%, 5%, 6%, 7%, 8%, 9%, 10%, 11%, 12%, 13%, 14%, 15%, 16%, 17%, 18%, 19%, 20%, or a range between any two of the above values, or any non-integer value within the aforementioned range of 0-20%. Disclosed herein are beneficial effects of using nucleic acid molecules having a kb length that is, is about, is less than, is greater than, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, or more than 179 kb, or a range between any two of the above values, or any non-integer value greater than 150 kb. Disclosed herein are further beneficial effects of using nucleic acid molecules having a kb length that is, is about, is less than, is greater than, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, or greater than 300, or a range between any two of the above values, or any non-integer value greater than 180 kb. Also disclosed herein are beneficial effects of practicing the methods herein wherein a combination of 2, 3, 4, or 5 of the beneficial parameters herein, or combinations of at least 1 of the beneficial parameters disclosed herein with at least one of the further beneficial parameters herein, such that more than one of the beneficial parameters selected above or at least one of the beneficial parameters and at least one of the further beneficial parameters are followed simultaneously.

Parameters may be optimized for a given sample or for a given analysis. For example, assembly can be maximized with respect to contig length by reducing stringency of assembly. For example, by decreasing the alignment threshold (P-value), one will get more alignments between molecule pairs and between molecules and contigs. More pairing will generally lead to more and longer assembled contigs, as measured by better genome coverage ratio and larger contig N50. Reducing minimal coverage for an extension/merge step will exhibit a similar effect. Decreasing minimal molecule length for assembly will also lead to longer contigs due to higher genome coverage. Alternately, if a user is more interested in assembly accuracy, one can increase the alignment threshold, increase minimal molecule length required to participate in assembly and increase minimal coverage for assembly steps. The assembler will be less likely to make errors, at the same time, it may not assemble complete in regions where coverage is low or label density is low.

As an illustrative example, of the beneficial effects of optimal parameters as disclosed herein, the relative effects of input DNA fragment size on assembly parameters was determined. Human genomic DNA was nicked with Nt.BspQI nicking endonuclease. The nicked DNA was labeled with Taq polymerase by nick translation using Atto dUTP and the nicks repaired with ligase. The labeled DNA was stained with YOYO-1 for processing on the Irys system (BioNano Genomics, described at http://www.bionanogenomics.com/products/). Briefly, DNA was linearized in massively parallel nanochannels, excited with the appropriate lasers for backbone label and nick label detection, and optically imaged to reveal the pattern of labels on DNA molecules. The labeled DNA molecules were mapped against the reference genome to determine labeling efficiency and other assembly parameters. The input human DNA was found to have a stretch factor of 85%, a stretch variability of 0.2, a label density of 10.3 per 100 kb, a map rate of 71%, a false-positive of 11% and a false negative of 15%.

Figure 2:
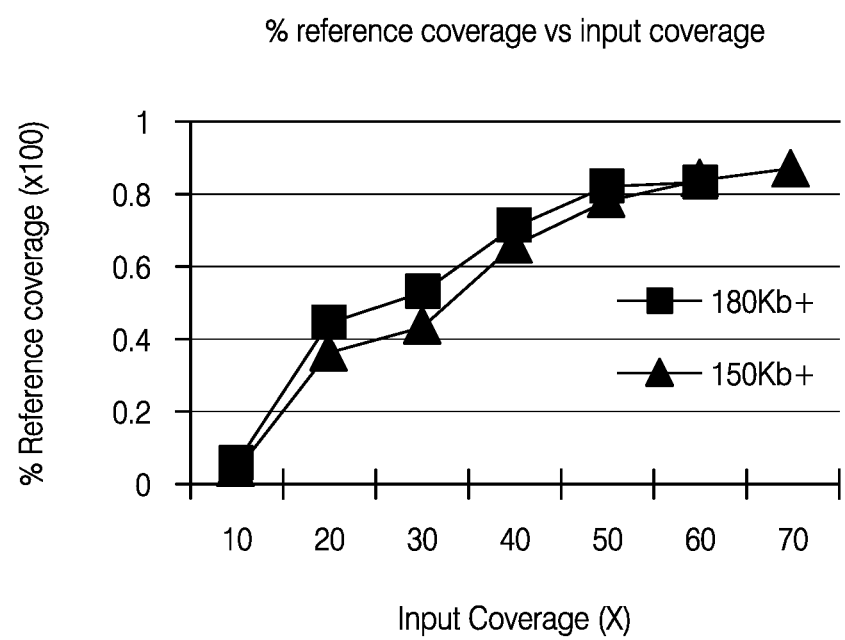
FIG. 2 depicts percent reference coverage as a function of fold input coverage for samples having a minimum fragment size of 150 kb and 180 kb.
Figure 3:
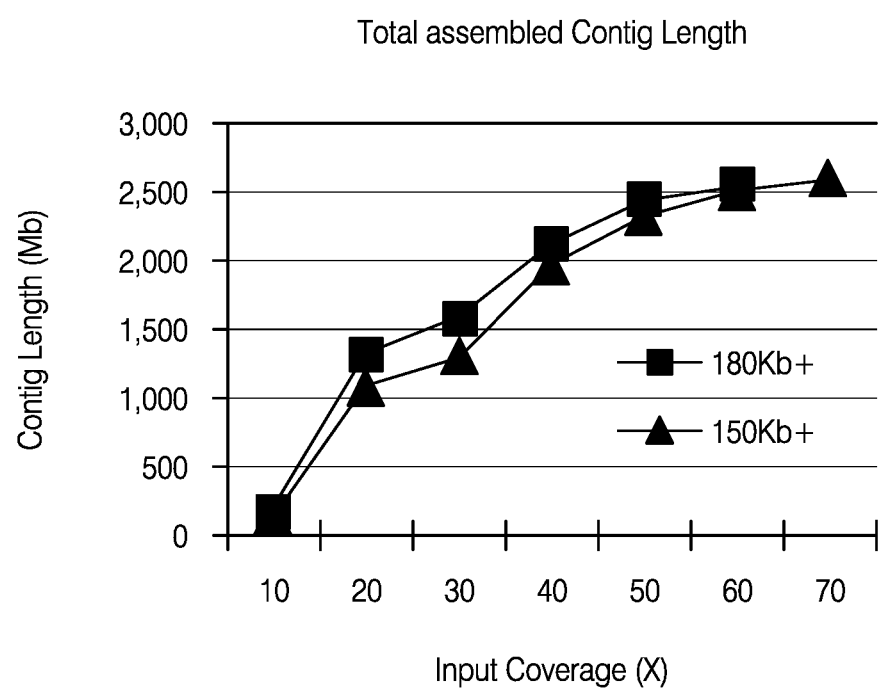
FIG. 3 depicts total assembled contig length in Megabases as a function of fold input coverage for samples having a minimum fragment size of 150 kb and 180 kb.

DNA molecules >150 Kb or >180 Kb were independently assembled to produce genome maps. FIG. 1 depicts contig N50 as a function of reference genome input coverage, expressed as multiples of haploid human genome (~3.2 Gb). FIG. 2 depicts percent reference genome coverage as a function of input coverage. FIG. 3 depicts total assembled contig length as a function of input coverage. Contig N50 is a measurement of distribution of contig size where total length of contigs with size >N50 is half of the total contig length. Total contig length equals the sum of consensus length of all contigs.

As indicated in FIG. 1, for a given contig input coverage, an input DNA sample of fragments equal to or greater than 180 kb consistently yields assembled contigs of an average size greater than that of assembled contigs observed for an input DNA sample comprising fragments of as small as 150 kb or greater. This result indicates the unexpected benefit of an input sample minimum fragment size of 180 kb relative to 150 kb in relation to average assembled contig size.

As indicated in FIG. 2, for a given contig input coverage, an input DNA sample of fragments equal to or greater than 180 kb consistently yields a percent reference coverage greater than that of assembled contigs observed for an input DNA sample comprising fragments of as small as 150 kb or greater. This phenomenon is particularly evident for input coverage ranges of 50× or less, as at greater coverage values the percent reference coverage appears to approach an asymptote for both fragment size samples. This result indicates the unexpected benefit of an input sample minimum fragment size of 180 kb relative to 150 kb in relation to percent of reference coverage achieved by the assembled contigs, particularly for input coverage of 50× or less, but also generally independent of input coverage.

Similarly, as indicated in FIG. 3, for a given contig input coverage, an input DNA sample of fragments equal to or greater than 180 kb consistently yields a contig length greater than that of assembled contigs observed for an input DNA sample comprising fragments of as small as 150 kb or greater. This phenomenon is particularly evident for input coverage ranges of 50× or less, as at greater coverage values the contig length appears to approach an asymptote for both fragment size samples. This result indicates the unexpected benefit of an input sample minimum fragment size of 180 kb relative to 150 kb in relation to assembled contig length achieved, particularly for input coverage of 50× or less, but also generally independent of input coverage.

Beneficial Effects of Methyltrasferase Mediated Sequence-Specific DNA Labeling in Combination with the Assembly Parameters Disclosed Herein.

Sequence-specific single-strand nicking enzymes have been used to generate free 5' and 3' ends of individual single strands of double-stranded DNA. These free single-stranded ends are then available for labeling, for example via extension form the nicked 3' end of a single-strand, using the intact complementary strand as a template to direct base incorporation. By providing labeled bases, one may effect labeling of a double-stranded DNA molecule at sites of specific nucleic acid sequence. After a certain amount of label incorporation, the extension reaction may be stopped and the translated nick repaired, for example using the cell's own machinery. The result of the reaction is a double-stranded nucleic acid molecule having a label incorporated at a specific sequence wherever that sequence occurs throughout the molecule.

Single-strand nicking is an effective method of labeling specific nucleic acid sequence in a nucleic acid molecule. However, while the labeling is occurring at a nick site, nicked labeling intermediates are held together by a single strand at that site. As single-stranded regions are substantially more fragile than double stranded nucleic acid molecules, it is not uncommon for these regions to break during the labeling process. This is a particularly critical issue when long nucleic acid molecules are preferred, such as molecules of 150 kb or greater, or even molecules of 180 kb or greater, or when a particularly densely occurring sequence is to be labeled, such as a sequence which occurs 5-35 times per 100 kb, 5-25 times per 100 kb, or 7-15 times per 100 kb.

As indicated herein, for example in FIGS. 1, 2, and 3, it is demonstrated that there is a measurable benefit to providing an input sample having a greater minimum fragment length. Accordingly, although nick labeling, methyltransferase labeling and additional sequence-specific labeling techniques are consistent with the disclosure herein, there is an unexpected benefit to providing samples of a longer DNA fragment size.

By employing a DNA labeling method such as methyltransferase labeling, which leaves the labeled DNA fragment intact (that is, labeling at least one motif repeated throughout a first genome with at least one label, wherein the labeling maintains integrity of each strand of the double-stranded DNA) rather than using a labeling technique which transiently breaks the phosphate backbone of one strand in double-stranded DNA to form intermediates held together by one or more single-stranded segments (as occurs with nick labeling), one is more able to make use of the beneficial effects of larger input sample fragment size on contig assembly as indicated in FIGS. 1, 2 and 3.

Accordingly, some embodiments provide methods and compositions that label specific nucleic acid sequences without temporarily compromising strand integrity or strand phosphodiester bond integrity.

Through the methods, compositions and devices disclosed herein, one may determine the presence of sequence-specific motifs within DNA molecules of measured length, and assemble these molecules into a reference contig up to and including a whole genome map. Such information may be used, for example, to identify repeat-mediated genome structural polymorphisms, such as those driven by di- or tri-nucleotide repeats, to accurately measure the size of regions of draft genomes for which primary sequence information cannot be determined due to, for example, the presence of highly repetitive sequence, to determine the size and extent of simple or complex transposon or retroviral insertion sites, or to determine the presence and extend of genome rearrangements, such as those which are associated with diseases such as various human cancers.

As defined herein, Stretching DNA means a reduction of the entropy of the DNA structure by one of several techniques including the use of nanochannel confinement. See, for example U.S. Pat. No. 7,217,562, published May 15, 2007, the contents of which are hereby expressly incorporated by reference in their entirety.

As defined herein, Stretch variability is calculated as the standard deviation of bpp (base pair per pixel) of each mapped molecule. The bpp is number of reference bases divided by measured length, aka base per pixel.

As defined herein, persistence length of DNA is the length at which the time-average angle made by the two ends of an intrinsically straight DNA molecule is 57 Degrees. See, for example, *Understanding DNA: The Molecule and How it Works*, by Chris R. Calladine, Horace Drew; Ben Luisi, Andrew Travers, Academic Press Mar. 13, 2004; he contents of which are hereby explicitly incorporated by reference in their entirety.

As defined herein, an error rate corresponds to False Positive or False Negative result when labeled molecules are aligned against a reference genome (no assembly of labeled DNA is needed).

As defined herein, Stretch variability is calculated as the standard deviation of bpp (base pair per pixel) of each mapped molecule. The bpp is number of reference bases divided by measured length, aka base per pixel.

EXAMPLES

Example 1

Labeling with Fluorescent SAM

Megabase containing human DNA is treated with a methyltransferase (MTase) selected from table 1 in the presence of a modified S-adenosyl methionine (SAM) comprising a fluorophore or multiple fluorophores. Following covalent transfer of the fluorophore-SAM complex to the methyltransferase target site, the labeled DNA is stained with yoyo I for processing on the Irys system (BioNano Genomics). Briefly, DNA is linearized in massively parallel nanochannels to achieve ~80% stretching, excited with the appropriate lasers for backbone and labels detection, and optically imaged to reveal the pattern of labels on DNA molecules. MTase labeling conditions are adjusted to achieve >40% mapping to the reference genome with an error rate <20%. Molecules ≥150 Kb are interrogated for overlap mapping to generate a genome map.

Example 2

Labeling with Click (Alkyne-Azide-Cu-Ligand)

Megabase containing human DNA is treated with a methyltransferase selected from table 1 in the presence of a modified S-adenosyl methionine (SAM) comprising an alkyne transfer moiety. Following covalent transfer of the alkyne group to the methyltransferase target site, the alkyne tagged sites are fluorescently labeled using a copper-catalyzed coupling reaction in the presence of a copper-coordinating ligand (e.g., BTTAA, BTTES) to prevent copper induced DNA fragmentation. The labeled DNA is stained with yoyo I for processing on the Irys system as described for Example 1.

Example 3

Labeling with Click (Azide-DBCO)

Megabase containing human DNA is treated with a methyltransferase selected from table 1 in the presence of a modified S-adenosyl methionine (SAM) comprising an azide transfer moiety. Following covalent transfer of the azide group to the methyltransferase target site, the azide tagged sites are fluorescently labeled with a DBCO-fluorophore conjugate (copper free click chemistry). The labeled DNA is stained with yoyo I for processing on the Irys system as described for example I. Examples of DBCO-fluorophore conjugates include direct coupling of DBCO to a fluorophore or coupling DBCO to a moiety which is coupled to multiple fluorophores (e.g., DBCO oligo or dendrimer comprising multiple fluorophores).

Example 4

Labeling with Click (DBCO-Azide)

Megabase containing human DNA is treated with a methyltransferase selected from table 1 in the presence of a modified S-adenosyl methionine (SAM) comprising a DBCO transfer moiety. Following covalent transfer of the DBCO group to the methyltransferase target site, the DBCO tagged sites are fluorescently labeled with an azide-fluorophore conjugate (copper free click chemistry). The labeled DNA is stained with yoyo I for processing on the Irys system as described for example 1. Examples of azide-fluorophore conjugates include direct coupling of azide to a fluorophore or coupling azide to a moiety which is coupled to multiple fluorophores (e.g. DBCO oligo or dendrimer comprising multiple fluorophores).

Example 5

Labeling of T7 DNA

A solution (40 ul) of 2 uL T7 DNA (500 ng/ul), M.BseCI (285 nM) and Atto532AdoY (40 uM) in 10 mM Tris-HCl, 10 mM EDTA, and 5 mM β-mercaptoethanol, pH 7.4 were mixed with 4 uL NaOH (0.1M). The solution was incubated for 5 h at 55° C. Proteinase K (1 ul) was added and the solution incubated for 1 h at 37° C. DNA was ethanol precipitated and redissolved in 1×TE buffer (10 ul).

Figure 4:
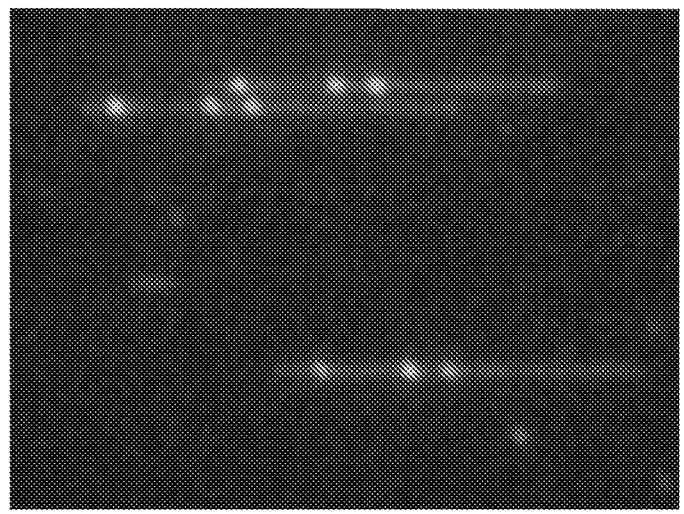
FIG. 4 shows single T7 DNA molecules (blue) visualized in IrysChip™ nanochannel arrays. The green dots represent M.BseCI recognition sequences (ATCGAT) labeled with the Atto532 dye. T7 DNA contains three M.BseCI recognition sequences.

An image of single labeled T7 DNA molecules is presented in FIG. 4. Single T7 DNA molecules (blue) were visualized in IrysChip™ nanochannel arrays. The green dots represent M.BseCI recognition sequences (ATCGAT) labeled with the Atto532 dye. T7 DNA contains three M.BseCI recognition sequences.

Example 6

Imaging of Labeled T7 DNA

For DNA staining of the T7 DNA labeled in Example 5, above, a solution (50 ul) of DNA (100 ng/ul), YOYO-1 (500 nM) in 1× flow buffer was incubated for 4 h at 4° C. Subsequently, a freshly prepared solution (4 ul) of 4-nitrobenzoic alcohol (1.4 mM), Trolox (1.4 mM), protocatechuate-3,4-dioxygenase (0.36 uM), protocatechuic acid (50 ug) was mixed with 10 uL of the stained DNA (above) and was loaded onto an IrysChip™ and imaged using the Irys™ instrument. FIG. 4 represents an example of imaged, labeled T7 DNA molecules.

Example 7

Labeling of *E. coli* DNA

A solution (40 ul) of *E. coli* DNA (500 ng), M.BseCI (22× excess over DNA sites) and Atto532AdoY (40 uM) in 10 mM Tris-HCl, 10 mM EDTA, and 5 mM beta-mercaptoethanol, pH 7.4 were mixed with 4 uL NaOH (0.1M). The solution was incubated for 5 h at 55° C. Proteinase K (1 ul) was added and the solution incubated for 1 h at 37° C. The DNA was dialyzed against 1×TE buffer and stained with YOYO-1 to a final concentration of 3.5-5 ng/ul.

Example 8

Imaging of Labeled E. coli DNA

A freshly prepared solution (4 ul) of 4-nitrobenzoic alcohol (1.4 mM), Trolox (1.4 mM), protocatechuate-3,4-dioxygenase (0.36 uM), protocatechuic acid (50 ug) was mixed with stained E. coli DNA of Example 7, 1x flow buffer and Tris (25 mM) and NaCl (10 mM) were added. The sample was loaded onto an IrysChip™ and imaged using the Irys™ instrument.

Example 9

Assembly of Labeled E. coli DNA into a Contig

Figure 5:
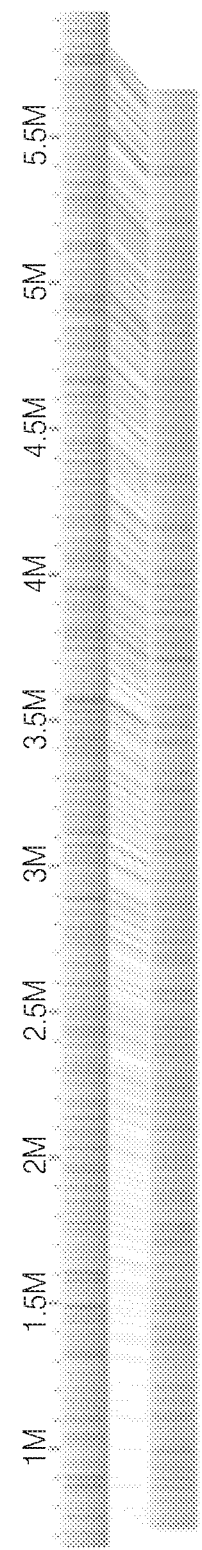
FIG. 5 shows an exemplary alignment of an assembled T7 contig (right vertical bar) to a reference contig (left vertical bar). Vertical or slanted lines connect homologous sequence among the two contigs.

The E. coli DNA of Examples 7 and 8 was assembled and compared to a reference genome. The results are presented in FIG. 5. The labeled E. coli DNA assembled into a single contig (FIG. 5, right contig) and aligned to a reference contig sequence (FIG. 5, left contig). The results indicate that the E. coli DNA analyzed herein contains a number of deletions, in combination totaling approximately 0.2-0.3 Mb, located at three or more positions throughout the analyzed E. coli DNA relative to the reference.

Example 10

Assembly of Labeled Human Chromosome 17 DNA into a Contig

Human chromosome 17 DNA was labeled and visualized, and the resulting DNA fragment size and sequence information was used to assemble a contig that was compared to previously existing chromosome 17 sequence information.

Figure 6:
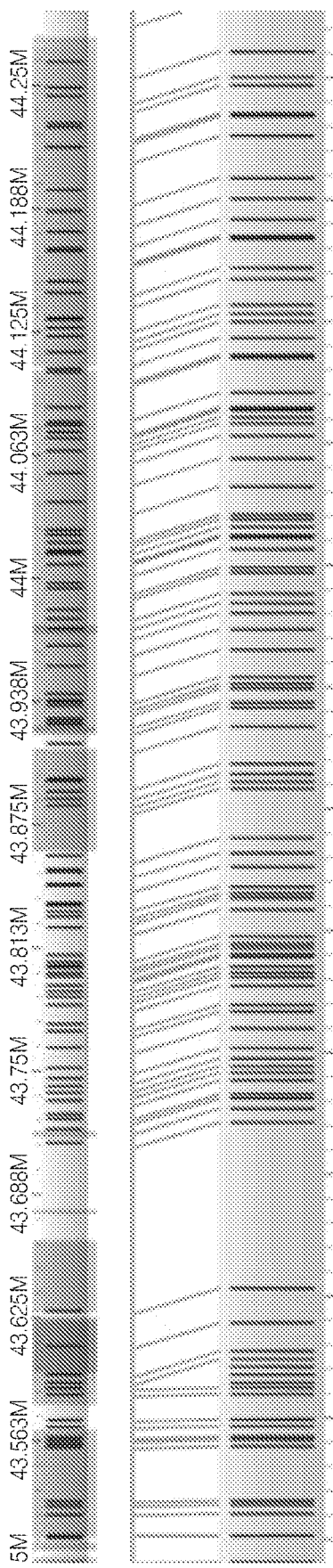
FIG. 6 shows an exemplary alignment between a region of human chromosome 17 reference contig (top) and an assembled chromosome 17 contig (bottom). Grey lines between the reference contig and the assembled contig indicate correlated sequence motifs.

FIG. 6A indicates the reference chromosome contig, with markers indicated as horizontal bars accompanied by DNA Megabase (Mb) indications. FIG. 6B indicates the results of a comparison between the assembled contig and the reference contig of FIG. 3A.

Grey lines between the two contig cartoons indicate correlated sequence motifs. The assembled contig is found to harbor a single insertion near the left end of the alignment as presented. The insertion is recognized by a shift to the right of it from vertical lines connecting the assembled contig to the reference contig, to diagonal lines after the insertion site, reflecting the presence of the insertion sequence.

Example 11

Analysis of Optimization Parameters: Fragment Length

Human genomic DNA was nicked with Nt.BspQI nicking endonuclease. The nicked DNA was labeled with Taq polymerase by nick translation using Atto dUTP and the nicks repaired with ligase. The labeled DNA was stained with yoyo I for processing on the Irys system (BioNano Genomics). Briefly, DNA was linearized in massively parallel nanochannels, excited with the appropriate lasers for backbone and labels detection, and optically imaged to reveal the pattern of labels on DNA molecules. DNA molecules >150 Kb or >180 Kb were independently assembled to produce genome maps. FIG. 1 depicts contig N50 as a function of reference genome input coverage, expressed as multiples of haploid human genome (~3.2 Gb). FIG. 2 depicts percent reference genome coverage as a function of input coverage. FIG. 3 depicts total assembled contig length as a function of input coverage. Contig N50 is a measurement of distribution of contig size where total length of contigs with size >N50 is half of the total contig length. Total contig length=sum of consensus length of all contigs.

Example 12

Analysis of Optimization Parameters: Sample Input Amount

Decreasing amount of Human genomic DNA was nicked with Nt.BspQI nicking endonuclease to simulate over-nicking. The nicked DNA was labeled with Taq polymerase by nick translation using Atto dUTP and the nicks repaired with ligase. The labeled DNA was stained with yoyo I for processing on the Irys system (BioNano Genomics). An increase in false positive (FP) rate was noted that correlates with poor reference mapping leading to poor assembly. That is, the false positive rate increased with decreasing amounts of input DNA.

Example 13

Analysis of Optimization Parameters: Correlation of False Negative Values and Assembly Quality Decreasing amount of Human genomic DNA was nicked with Nt.BspQI nicking endonuclease to simulate over-nicking. The nicked DNA was labeled with Taq polymerase by nick translation using Atto dUTP and the nicks repaired with ligase. The labeled DNA was stained with yoyo I for processing on the Irys system (BioNano Genomics). An increase in FP rate was noted that correlates with poor reference mapping leading to poor assembly. That is, the false positive rate increased with decreasing amounts of input DNA. The results are presented in Table 3, indicating DNA sample mass, center of mass, label density, map rate, percent false-positive (% FP) and percent false-negative (% FN) for a range of DNA mass samples.

TABLE 3

| Human cell line DNA | Center of Mass | Label/ 100 Kb | Map rate (SNR > 3.0) | % FP | % FN |
|---|---|---|---|---|---|
| 600 ng DNA | 176 | 14.83 | 25.8% | 27.4 | 9.7 |
| 780 ng DNA | 204 | 13.88 | 36.9% | 29.4 | 8.7 |
| 1080 ng DNA | 189 | 12.14 | 57.7% | 22.8 | 10.4 |
| 1260 ng DNA | 210 | 12.04 | 65.3% | 20.7 | 9.9 |
| 1440 ng DNA | 210 | 11.62 | 66.9% | 17.4 | 10.5 |

Genomic DNA isolated from human blood samples was nick labeled repaired and interrogated on the Irys™ system. An increase in FN rate correlated with decrease reference mapping leading to poor assembly. That is, an increase in the false negative rate correlated with a decrease in the map rate. The results are presented in Table 4, indicating map rates, false-positive rates (% FP) and false-negative rates (% FN) for a number of blood DNA samples.

TABLE 4

|  | COM | Map Rate | % FP | % FN |
|---|---|---|---|---|
| Blood DNA | 140 | 39.4% | 5.5 | 24 |
| Blood DNA | 128 | 42.8% | 4.8 | 20.1 |
| Blood DNA | 204 | 51.0% | 4.5 | 18.8 |
| Blood DNA | 195 | 51.4% | 5.8 | 17.1 |
| Blood DNA | 205 | 61.7% | 6.1 | 16.6 |
| Blood DNA | 197 | 57.1% | 5.2 | 14.7 |

Example 14

Analysis of Optimization Parameters: Conditions Favoring Genome Assembly in the Presence of a Reference Genome Conditions that favor good genome assembly were empirically determined based on the presence of a representative reference map. Uniform stretching to ~85% with minimal stretch variability <20% along with efficient labeling and 2 kb image resolution benefit reference mapping to support de novo genome assembly. Results were improved for molecules >150 kb, preferably >180 kb. Improving image resolution, increasing information density (for example, multiple colors), such that overlap region between pair wise lined molecule represent a unique genome pattern, decrease size dependence.

Example 15

Analysis of Optimization Parameters: Conditions Favoring Genome Assembly in the Presence of a Reference Genome for Complex Genomes In the case of complex genomes, as in human, especially if dealing with cancerous material or even cultured cells, genetic divergence from existing reference genome can be high such that reference mapping may be more challenging.

Nonetheless, de novo assembly was still obtained, as documented by successful assembly of human genomes with a reference map rates ranging from 40-70% pending DNA source. Uniform stretching to ~85% with minimal stretch variability <20% along with efficient labeling and 2 kb image resolution benefit reference mapping to support de novo genome assembly. Results were improved for molecules >150 kb, preferably >180 kb. Improving image resolution, increasing information density (for example, multiple colors), such that overlap region between pair wise lined molecule represent a unique genome pattern, decrease size dependence.

Example 16

Analysis of Optimization Parameters: Conditions Favoring Genome Assembly in the Absence of a Reference Genome In the absence of a reference genome map, parameters for successful de novo assembly can rely on maximal pairwise assembly with depth of coverage, for example in the following manner. First the alignment ratio between molecules is measured. The calculation of alignment ratio is similar to that of map rate. The molecules are aligned to each other instead of aligning them to a reference genome. Then the average number of alignment per input molecule is divided by expected coverage of genome to get the alignment ratio. Calculation may require a good estimation of sample genome size, which is typically true.

As an alternative, input molecules quality is estimated by investigating a histogram of p-values of pair-wise alignments. The peak of the p-value histogram and its standard deviation will serve as a good proxy for molecule quality. Input molecules consistent with each other will generate a higher peak p-value.

What is claimed is:

1. A method of characterizing a first nucleic acid sample to interrogate a genomic region without compromising strand phosphodiester bond integrity, comprising:
   covalently labeling a plurality of nucleic acid molecules in the first nucleic acid sample at at least one repeated motif with a first label, wherein the covalent labeling maintains integrity of the plurality of nucleic acid molecules, wherein no phosphodiester bond is broken through said covalent labeling, wherein the at least one repeated motif is a methyltransferase recognition sequence, wherein labeling is effected with a methyltransferase and a modified cofactor, wherein the genomic region is at least about 4 Mb, and wherein the labeled nucleic acid molecules have a length of at least 150 kb;
   marking the plurality of nucleic acid molecules in the first nucleic acid sample with a second label, wherein the second label is distinct from the first label;
   linearizing the plurality of nucleic acid molecules by passing the plurality of nucleic acid molecules into at least one nanochannel;
   detecting the first label and the second label to produce patterns of the at least one repeated motif of the plurality of nucleic acid molecules;
   assembling the patterns of the at least one repeated motif of the plurality of nucleic acid molecules to construct a first map of the genomic region; and
   comparing the first map of the genomic region to a second map of the genomic region, wherein said second map is of a reference genome, wherein the reference genome comprises sequence information that is stored digitally, and wherein the comparing comprises in silico analysis,
   wherein the at least one repeated motif has an average repeat frequency of about 7 sites to about 15 sites per 100 Kb in the genomic region and wherein the strand phosphodiester bonds of the plurality of nucleic acid molecules are intact.

2. The method of claim 1, wherein the second label is a nonspecific nucleic acid label.

3. The method of claim 1, wherein the modified cofactor comprises a transferable tag which becomes covalently coupled to the methyltransferase recognition sequence.

4. The method of claim 1, wherein the modified cofactor comprises a detectable tag.

5. The method of claim 3, wherein the transferable tag is selected form the group consisting of a fluorophore, a hapten, streptavidin, avidin, neutravidin, biotin, a stabilized reactive group a radiolabel, an electromagnetic label, an azide, Dibenzocyclooctyne (DBCO), and an alkyne.

6. The method of claim 4, wherein the detectable tag is selected form the group consisting of a fluorophore, a hapten, streptavidin, avidin, neutravidin, biotin, a stabilized reactive group, a radiolabel, an electromagnetic label, an azide, Dibenzocyclooctyne (DBCO), and an alkyne.

7. The method of claim 1, wherein the nucleic acid molecules correspond to at least 20 fold coverage of the genomic region.

8. The method of claim 1, further comprising:
labeling a plurality of nucleic acid molecules in a second nucleic acid sample at the same repeated motif, wherein the labeling maintains integrity of the plurality of nucleic acid molecules;
marking the plurality of nucleic acid molecules in the second nucleic acid sample with the second label;
linearizing the plurality of nucleic acid molecules in the second nucleic acid sample by passing the plurality of nucleic acid molecules into at least one nanochannel;
detecting the first label and the second label to produce patterns of the at least one repeated motif of the plurality of nucleic acid molecules from the second nucleic acid sample; assembling the patterns of the at least one repeated motif of the plurality of nucleic acid molecules to construct a second map of the genomic region; and
comparing the first map to the second map to ascertain a similarity or difference between the first nucleic acid sample and the second nucleic acid sample.

9. The method of claim 1, comprises assembling the patterns of the at least one repeated motif of at least 100, at least 1,000, at least 1,000 or more nucleic acid molecules.

10. A method of analyzing a nucleic acid in a genomic region for a sequence structure without compromising phosphodiester bond integrity in the nucleic acid, the method comprising the steps of
a) introducing a first label at a plurality of occurrences of a recognition site of the nucleic acid to generate a covalently-bound sequence-specific label at the plurality of occurrences of the recognition site, wherein no phosphodiester bond is broken through said introducing the first label to the nucleic acid, wherein said introducing the first label comprises contacting said nucleic acid with a molecule having methyltransferase activity, wherein the genomic region is at least about 4 Mb, and wherein the labeled nucleic acid molecules have a length of at least 150 kb;
b) labeling the nucleic acid with a second label;
c) passing the nucleic acid into a nanochannel to hold the nucleic acid in an elongated state;
d) detecting the first label to identify a pattern of the recognition site;
e) detecting the second label;
f) assembling the pattern of the recognition site of the nucleic acid to construct a first map of the genomic region; and
g) comparing the first map of the genomic region to a second map of the genomic region, wherein said second map is of a reference genome, wherein the reference genome comprises sequence information that is stored digitally, and wherein the comparing comprises in silico analysis,
wherein the plurality of occurrences of the recognition site has an average repeat frequency of about 7 sites to about 15 sites per 100 Kb in the nucleic acid and wherein the phosphodiester bonds of the nucleic acid are intact.

11. The method of claim 10, wherein the second label is a non-sequence-specific label.

12. The method of claim 10, wherein the nucleic acid is a double-stranded DNA molecule.

13. A method of characterizing a first nucleic acid sample to interrogate a genomic region without compromising strand phosphodiester bond integrity, comprising:
covalently labeling a plurality of nucleic acid molecules in the first nucleic acid sample at at least one repeated motif with a first label, wherein the covalent labeling maintains integrity of the plurality of nucleic acid molecules, wherein no phosphodiester bond is broken through said covalent labeling, wherein the at least one repeated motif has an average repeat frequency of about 7 sites to about 15 sites per 100 Kb in the genomic region, wherein the genomic region is at least about 4 Mb, and wherein the labeled nucleic acid molecules have a length of at least 150 kb;
marking the plurality of nucleic acid molecules in the first nucleic acid sample with a second label, wherein the second label is distinct from the first label;
linearizing the plurality of nucleic acid molecules by passing the plurality of nucleic acid molecules into at least one nanochannel;
detecting the first label and the second label to produce patterns of the at least one repeated motif of the plurality of nucleic acid molecules;
assembling the patterns of the at least one repeated motif of the plurality of nucleic acid molecules to construct a first map of the genomic region; and
comparing the first map of the genomic region to a second map of the genomic region, wherein said second map is of a reference genome, wherein the reference genome comprises sequence information that is stored digitally, and wherein the comparing comprises in silico analysis,
wherein the strand phosphodiester bonds of the plurality of nucleic acid molecules are intact.

14. The method of claim 13, wherein the at least one repeated motif is a methyltransferase recognition sequence, and wherein labeling is effected with a methyltransferase and a modified cofactor.

15. The method of claim 14, wherein the modified cofactor comprises a transferable tag which becomes covalently coupled to the methyltransferase recognition sequence, wherein the transferable tag is selected form the group consisting of a fluorophore, a hapten, streptavidin, avidin, neutravidin, biotin, a stabilized reactive group a radiolabel, an electromagnetic label, an azide, Dibenzocyclooctyne (DBCO), and an alkyne.

16. The method of claim 14, wherein the modified cofactor comprises a detectable tag, wherein the detectable tag is selected form the group consisting of a fluorophore, a hapten, streptavidin, avidin, neutravidin, biotin, a stabilized reactive group, a radiolabel, an electromagnetic label, an azide, Dibenzocyclooctyne (DBCO), and an alkyne.

17. The method of claim 13, wherein the at least one repeated motif includes at least one binding site for a binding entity selected form the group consisting of a non-cutting restriction enzyme, a zinc finger protein, an antibody, a transcription factor, a transcription activator like domain, a DNA binding protein, a polyamide, a triple helix forming oligonucleotide, and a peptide nucleic acid; and wherein labeling is effected with the binding entity.

18. The method of claim 17, wherein the binding entity comprise at least one detectable tag selected form the group consisting of a fluorophore, a hapten, streptavidin, avidin, neutravidin, biotin, a stabilized reactive group, a radiolabel, an electromagnetic label, an azide, Dibenzocyclooctyne (DBCO), and an alkyne.

19. The method of claim 1, further comprising selecting the at least one repeated motif to be labeled having an average repeat frequency of about 5 sites to about 35 sites per 100 Kb in the genomic region.

20. The method of claim 1, wherein the labeled nucleic acid molecules have a length of at least 180 kb.

21. The method of claim 1, wherein the labeling is effected with a combination of at least two methyltransferases and a modified cofactor.

22. The method of claim 21, wherein the at least two methyltransferases are selected from the group consisting of Ml.Sapl/M2.Sapl, M.Ecal/M.BstEII, RM.Maql, RM.Sno506I, M.Smal/M.Cfr9I I MCphBI/M.Pac25I/M.TspMI/M.Xcyl I M.Xmal/M.Xvell, M.Kpnl, M.EcoRV, M.Spel, M.Nhel/M.Bmtl, M.ApaLI, M.BsaHI/M.HgiDi/M.HgiGI/M.HindV, RM.RdeGBI, M.CpeA VI/M.BstZl 71, M.Hpal, M.BamHI, M.Hincll and M.Hindll, M.MspAll, M.BbrUI/M.BloAI/M.Kasl/*M.MlaZV/M.PluTI/M.Sfol, M.Acll, M.BssSI, Ml.BsrBI/M2.BsrBI, M.BsaAI/*M.Ppu2 ll, RM.AspNLS2ORF1089P/RM.PspOMII, M.Haell/M.NgoAI/M.NgoBI, RM.RflFIII, and *M.Eco72I/M.Pm1I.

* * * * *